(12) United States Patent
Gupta et al.

(10) Patent No.: US 8,923,958 B2
(45) Date of Patent: Dec. 30, 2014

(54) SYSTEM AND METHOD FOR EVALUATING AN ELECTROPHYSIOLOGICAL SIGNAL

(75) Inventors: Sunny Gupta, Amherstview (CA); Mohsen Najafi Yazdi, Kingston (CA)

(73) Assignee: Analytics For Life Inc. (CA)

( * ) Notice: Subject to any disclaimer, the term of this patent is extended or adjusted under 35 U.S.C. 154(b) by 0 days.

(21) Appl. No.: 13/605,364

(22) Filed: Sep. 6, 2012

(65) Prior Publication Data
US 2013/0096394 A1     Apr. 18, 2013

Related U.S. Application Data

(63) Continuation-in-part of application No. PCT/US2012/024037, filed on Feb. 6, 2012.

(60) Provisional application No. 61/462,640, filed on Feb. 4, 2011.

(51) Int. Cl.
*A61B 5/0402* (2006.01)
*A61B 5/0476* (2006.01)
(Continued)

(52) U.S. Cl.
CPC ............. *A61B 5/04012* (2013.01); *A61B 5/044* (2013.01); *A61B 5/0452* (2013.01); *A61B 5/0245* (2013.01); *A61B 5/4848* (2013.01); *A61B 5/046* (2013.01); *A61B 5/0464* (2013.01); *A61B 5/02028* (2013.01); *A61B 5/055* (2013.01); *A61B 6/032* (2013.01); *A61B 5/7253* (2013.01); *A61B 5/7203* (2013.01); *A61B 5/04011* (2013.01); *A61B 5/04525* (2013.01); *G06K 9/0051* (2013.01); *G06K 9/00536* (2013.01); *A61B 5/4884* (2013.01); *A61B 5/7239* (2013.01); *A61B 5/7232* (2013.01)
USPC .......................................... 600/509; 600/544

(58) Field of Classification Search
None
See application file for complete search history.

(56) References Cited

U.S. PATENT DOCUMENTS 4,723,536 A    2/1988   Rauscher et al.
6,325,761 B1   12/2001  Jay
(Continued)

OTHER PUBLICATIONS

Efron, Bradley, et al., "Least Angle Regression," Annals of Statistics, vol. 32, No. 2, 2004, pp. 407-499.

(Continued)

*Primary Examiner* — Michael Kahelin
(74) *Attorney, Agent, or Firm* — Meunier Carlin & Curfman, LLC

(57) ABSTRACT

A method of evaluating an electrophysiological signal is disclosed. A mathematical reconstruction over at least one cycle of the electrophysiological signal is used to identify an abnormal substrate. A non-transitory computer readable medium is also disclosed. The nontransitory computer readable medium has stored thereon instructions for identifying a pathological substrate from a mathematical reconstruction of an electrophysiological signal, which, when executed by a processor, causes the processor to perform steps comprising using a mathematical reconstruction over many cycles of the electrophysiological signal to identify a pathological state. A system for evaluating an electrophysiological signal includes a processor configured to identify a pathological condition from a mathematical reconstruction of the electrophysiological signal. The system also includes a data input coupled to the processor and configured to provide the processor with the electrophysiological signal. The system further includes a user interface coupled to either the processor or the data input.

15 Claims, 24 Drawing Sheets
(11 of 24 Drawing Sheet(s) Filed in Color)

(51) Int. Cl.
*A61B 5/04* (2006.01)
*A61B 5/044* (2006.01)
*A61B 5/0452* (2006.01)
*A61B 5/0245* (2006.01)
*A61B 5/00* (2006.01)
*A61B 5/046* (2006.01)
*A61B 5/0464* (2006.01)
*A61B 5/02* (2006.01)
*A61B 5/055* (2006.01)
*A61B 6/03* (2006.01)
*G06K 9/00* (2006.01)

(56) References Cited

U.S. PATENT DOCUMENTS

2004/0059203 A1 3/2004 Guerrero et al.
2004/0230105 A1 11/2004 Geva et al.
2008/0027341 A1 1/2008 Sackner et al.
2009/0292180 A1 11/2009 Mirow

OTHER PUBLICATIONS

Mallat, Stéphane G, et al., "Matching Pursuits With Time-Frequency Dictionaries," IEEE Transactions on Signal Processing, vol. 41, No. 12, Dec. 1993, pp. 3397-3415.

International Search Report, dated Jun. 15, 2012, received in connection with corresponding International Patent Application No. PCT/US2012/024037.

Ki H. Chon, "Accurate Identification of Periodic Oscillations Buried in White or Colored Noise Using Fast Orthogonal Search", IEEE Transactions on Biomedical Engineering, vol. 48, No. 6, Jun. 2001.

Marica Kleniz and Thomas J. Osler, A Child's Gardent of Fractional Derivative'. The College Mathematics Journal, vol. 31, No. 2, 2000, pp. 82-887.

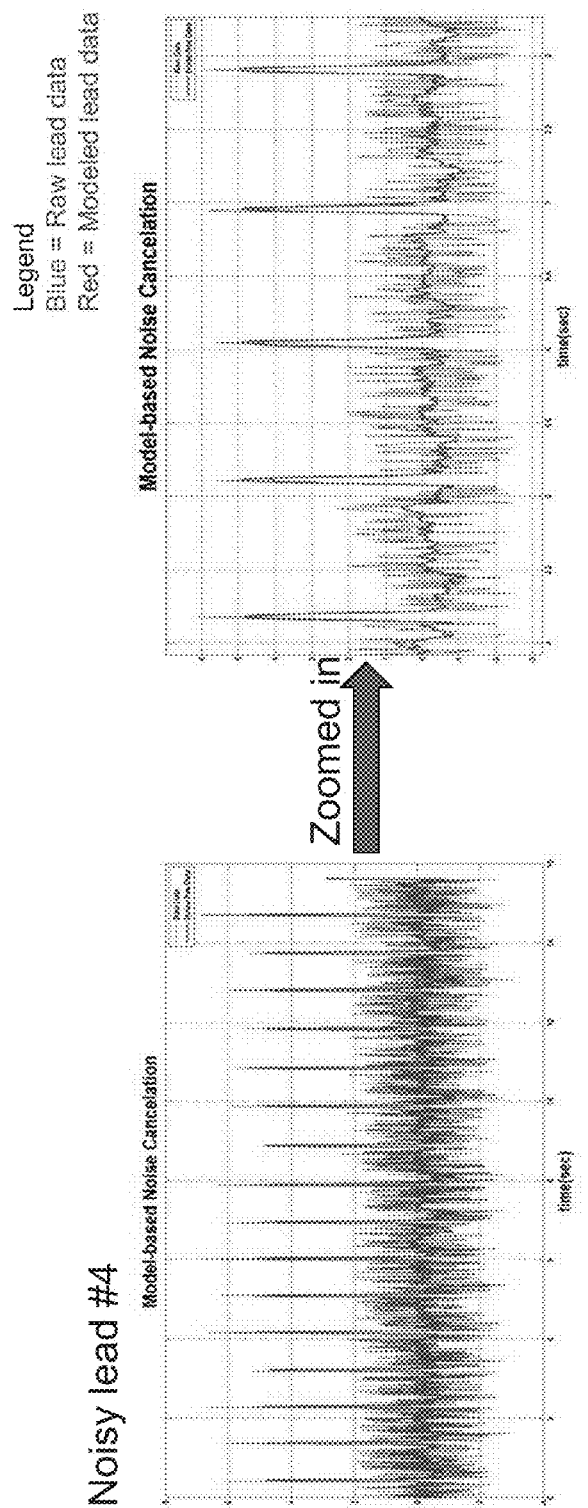

SYSTEM AND METHOD FOR EVALUATING AN ELECTROPHYSIOLOGICAL SIGNAL

RELATED APPLICATIONS

This application claims priority to PCT Application No. PCT/US2012/24037, filed Feb. 6, 2012, entitled "System and Method for Evaluating an Electrophysiological Signal," which claims priority to U.S. Provisional Application Ser. No. 61/462,640, filed Feb. 4, 2011, entitled "Phase Space and Enhanced Fast Orthogonal Search Used For Electrocardiogram Pathology Detection." The disclosures of the above-identified applications are hereby incorporated by reference in their entirety.

BACKGROUND

With the ongoing proliferation of data acquisition devices, more and more physiological aspects are able to be captured as electrophysiological signals. Some examples include, but are not limited to, gamma synchrony signals (based on electroencephalogram (EEG) measurements), a respiratory function signal, a pulse oximetry signal (measuring the oxygenation of a patient's blood), a perfusion data signal (measuring changes in tissue images following introduction of a contrast agent to the blood), and quasi-periodic biological signals.

Devices which capture electrophysiological signals may be valuable tools for physicians to study the health conditions of a patient. After the recording of the electrophysiological signal, it is up to the physician or healthcare provider to perform the signal analysis. For example, in the case of ECG signal analysis, there are certain integrated automatic analysis processes and systems which automatically determine different types of heart beats, rhythms, etc. The traditional output from the existing ECG software is basic data that often needs to be supplemented by an angiography or arteriography, Cardiac MRI (Magnetic Resonance Imaging), CT (Computed tomography) or a more invasive test. However, there are a number of limitations associated with all such systems described above, they are complex, their outputs are difficult to analyze, and such techniques are expensive to use.

In addition to the above systems, there are various time domain and frequency domain signal processing techniques which are being used for the analysis of electrophysiological signals to obtain more detailed information. Unfortunately, the time domain techniques are incapable of quantifying certain fluctuation characteristics of a number of pathologies related to the electrophysiological signal. For example, with regard to the heart, traditional methods for performing frequency-domain analysis of surface ECG signals, such as the Fourier transform, are limited since they do not address the beat-to-beat multi-lead variability in the morphology and phase of the entire ECG cycle over long consecutive time windows and the random nature of biological and electromagnetic noise or the variation between patients.

For example, in case of arrhythmia, the heart generates very complex ECG waveforms that have a large variation in morphologies. Dominant frequency analysis on these ECGs can be problematic since non-linear dynamic systems can appear to generate random noise. Discrete fast Fourier transforms and wavelet analysis have been shown experimentally to be incapable of detecting deterministic chaos in the presence of strong periodicity which tends to obscure the underlying non-linear structures. Thus, the detection of complex sub-harmonic frequencies which are thought to exist in all arrhythmia requires dynamic non-linear analyses. Complex subharmonic frequencies are similarly thought to exist in other types of electrophysiological signals and may be indicative of other pathological events which are not otherwise detectable from the electrophysiological signal using prior art methods.

SUMMARY

A method of evaluating an electrophysiological signal is disclosed. A mathematical reconstruction over at least one cycle of the electrophysiological signal is used to identify an abnormal substrate which may lead to pathological events.

A non-transitory computer readable medium is also disclosed. The non-transitory computer readable medium has stored thereon instructions for identifying an abnormal substrate from a mathematical reconstruction of an electrophysiological signal, which, when executed by a processor, causes the processor to perform steps comprising using a mathematical reconstruction over at least one cycle of the electrophysiological signal to identify a pathological conditions.

A system for evaluating an electrophysiological signal is also disclosed. The system includes a processor configured to identify a pathological substrate from a mathematical reconstruction of the electrophysiological signal. The system also includes a data input coupled to the processor and configured to provide the processor with the electrophysiological signal. The system further includes a user interface coupled to either the processor or the data input.

A method of evaluating an electrocardiogram (ECG) signal is further disclosed. The method may include receiving an electrophysiological signal; applying, using a processor of a computing device, a model-derived reconstruction using a summation series of complex exponentials over at least one cycle of the electrophysiological signal to identify a pathological substrate; and displaying, on a user interface, one or more indicators of the electrophysiological signal to represent at least a portion of the electrophysiological signal and the pathological substrate.

In accordance with other aspects, a method for applying a modified matching pursuit (MMP) transform to an electrophysiological signal is disclosed. The method may include receiving the electrophysiological signal at a computing device; generating, at the computing device, a plurality of non-linear terms corresponding to the electrophysiological signal; separating a noise component from the plurality of non-linear terms corresponding to the electrophysiological signal; and forming a reconstructed electrophysiological signal whereby the noise component is removed by using a subset of the plurality non-linear terms corresponding to the electrophysiological signal.

Other systems, methods, features and/or advantages will be or may become apparent to one with skill in the art upon examination of the following drawings and detailed description. It is intended that all such additional systems, methods, features and/or advantages be included within this description and be protected by the accompanying claims

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The components in the drawings are not necessarily to scale relative to each other. Like reference numerals designate corresponding parts throughout the several views.

FIGS. 15A and 15B show ECG signal data before and after noise removal;

DETAILED DESCRIPTION

There are numerous electrophysiological signals which may be captured from the body. Examples of electrophysiological signals include, but are not limited to an electrocardiogram (ECG), an electroencephalogram (EEG), a gamma synchrony signal, a respiratory function signal, a pulse oximetry signal, a perfusion data signal, a quasi-periodic biological signal, a fetal ECG, a blood pressure signal, and a heart rate signal. There is a proliferation of equipment for obtaining electrophysiological signals, but the ability of the prior art to identify pathological events from such signals has been limited as discussed above.

Embodiments of a method and system for evaluating an electrophysiological signal are disclosed herein. For convenience, the embodiments associated with FIGS. 1-9 will be discussed herein with respect to the evaluation of ECG electrophysiological signals; however, it should be understood by those skilled in the art that similar or equivalent embodiments may be applied to other types of electrophysiological signals.

Figure 1:
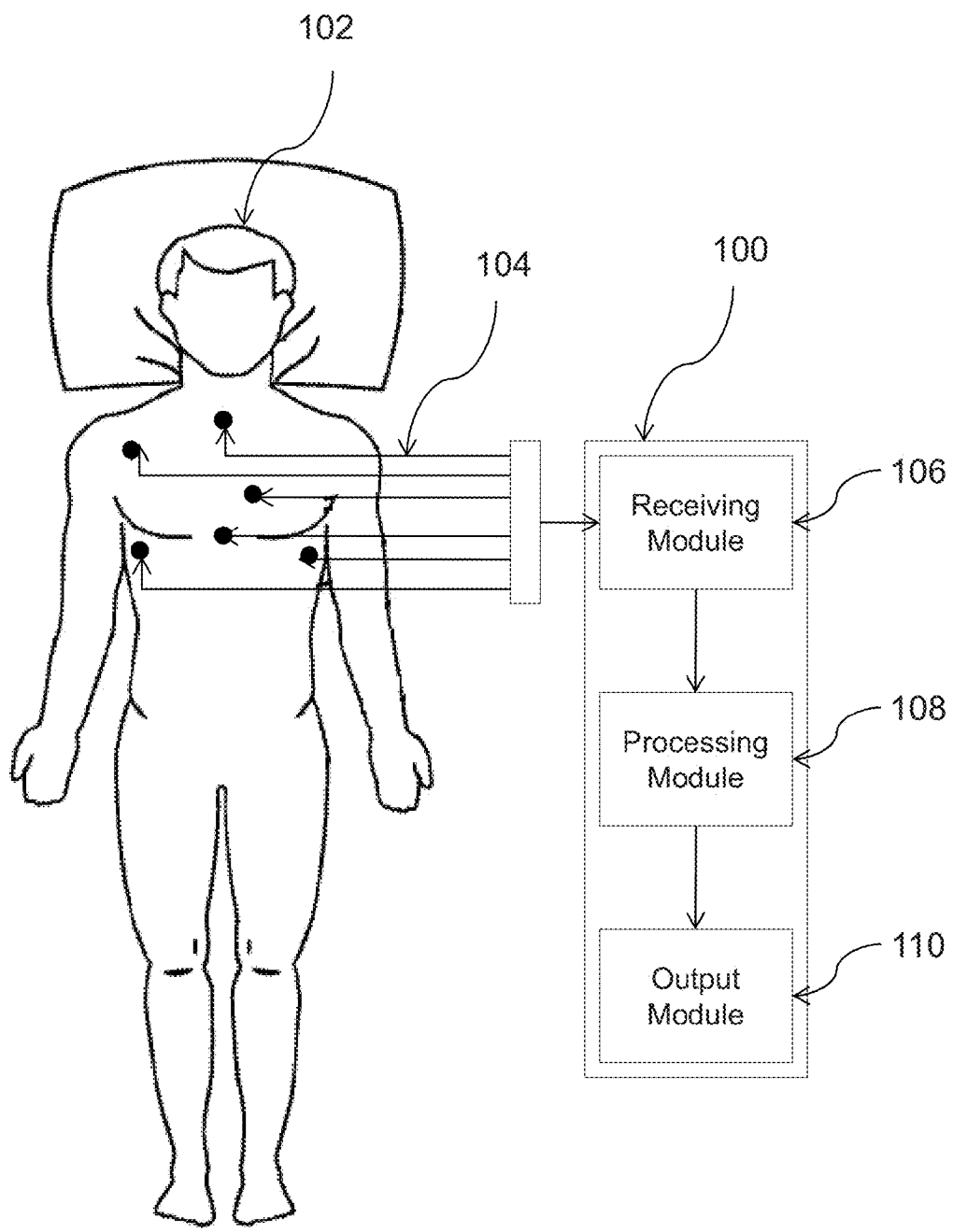
FIG. 1 is a block diagram depicting one embodiment of a system for evaluating an electrophysiological signal. In this embodiment, the electrophysiological signal comprises an ECG signal captured from a patient.

FIG. 1 schematically illustrates one embodiment of a system 100 which is used for the evaluation of ECG signal captured from a patient 102. In this embodiment, a plurality of electrodes 104 is placed over the patient's body to capture the ECG signal in three orthogonal channels mode. The ECG signals obtained from the plurality of electrodes 104 is collected by an electrophysiological signal capture device, for example a receiving module 106. In some embodiments, a Holter ECG monitor is used as the receiving module 66 for the recording of ECG signals. It should be appreciated that a person skilled in the art can also use any other method/device for the recording/capture of ECG signals. The recorded data from the ECG signal is made available to a processor 108 via a data input line. The processor 108 may include a computer, a laptop, a distributed computer system or network, an application specific integrated circuit (ASIC), a programmable logic array (PLA), a microprocessor, digital circuitry, analog circuitry, or any combination and/or plurality thereof which has been specifically configured or programmed to perform the described embodied evaluation actions described herein and their equivalents. It should be noted that the data processing techniques described herein are not possible by mental processes and that one or more of the disclosed steps requires transformation of data by the processor 108 such that it is more than just a mental step. In this embodiment, the processor 108 uses a Modified Matching Pursuit (MMP) for the processing of ECG data. The output of the processor 108 is then sent to a user interface/output module 110. The user interface 110 can be a display unit displaying the 3D phase space plot representation of the ECG data collected from the patient 102. As will be described further, the 3D phase plot can be used in some embodiments to help in locating the presence of complex sub-harmonic frequencies related to the abnormal conduction in the heart.

Figure 2:
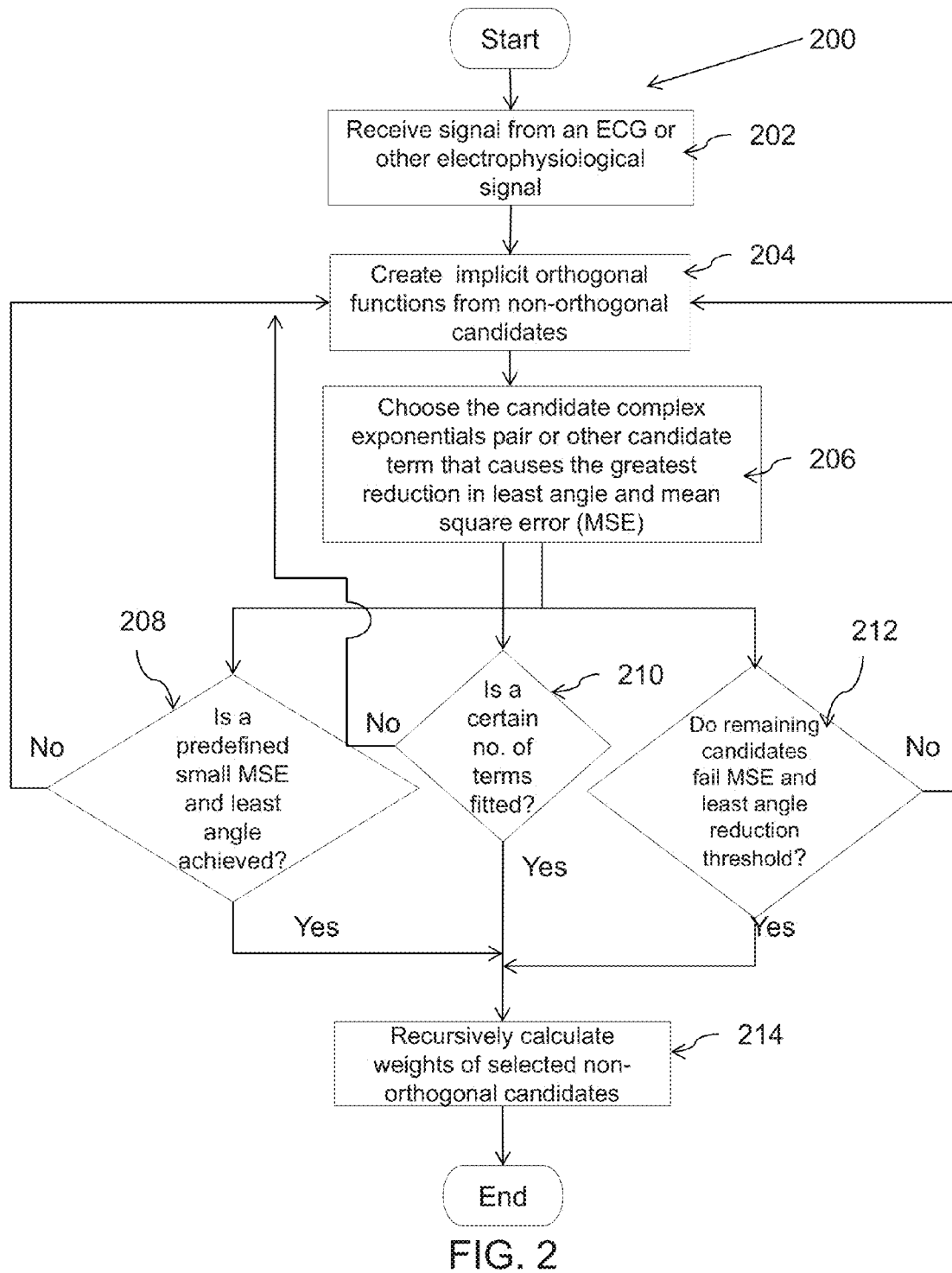
FIG. 2 is a flow diagram illustrating steps involved in one embodiment of a Modified Matching Pursuit (MMP) transformation in accordance with an embodiment of the present disclosure.

FIG. 2 is a flow chart 200 depicting the steps of one embodiment of a Modified Matching Pursuit using a least angle regression (LARS) process which may be used to produce a mathematical reconstruction of the ECG signal over a relatively large number of heartbeats (e.g., 1000 or more) according to some of the embodiments disclosed herein. A discussion of LARS may be found in Efron, Bradley; Hastie, Trevor; Johnstone, Iain and Tibshirani, Robert (2004), "Least Angle Regression", Annals of Statistics 32 (2): pp. 407-499, which is incorporated herein reference in its entirety. Least Angle Regression (LARS) relates to the classic model-selection method known as Forward Selection, or "forward stepwise regression." Given a collection of possible predictors, the one having largest absolute correlation with the response y is selected, e.g., and simple linear regression of y is performed on $x_{j1}$. This leaves a residual vector orthogonal to which is considered to be the response. The other predictors are projected orthogonally to $x_{j1}$ and the selection process is repeated. After k steps this results in a set of predictors $x_{j1}$, $x_{j2}$, . . . , $x_{jk}$ that are then used in the usual way to construct a k-parameter linear model.

Figure 21:
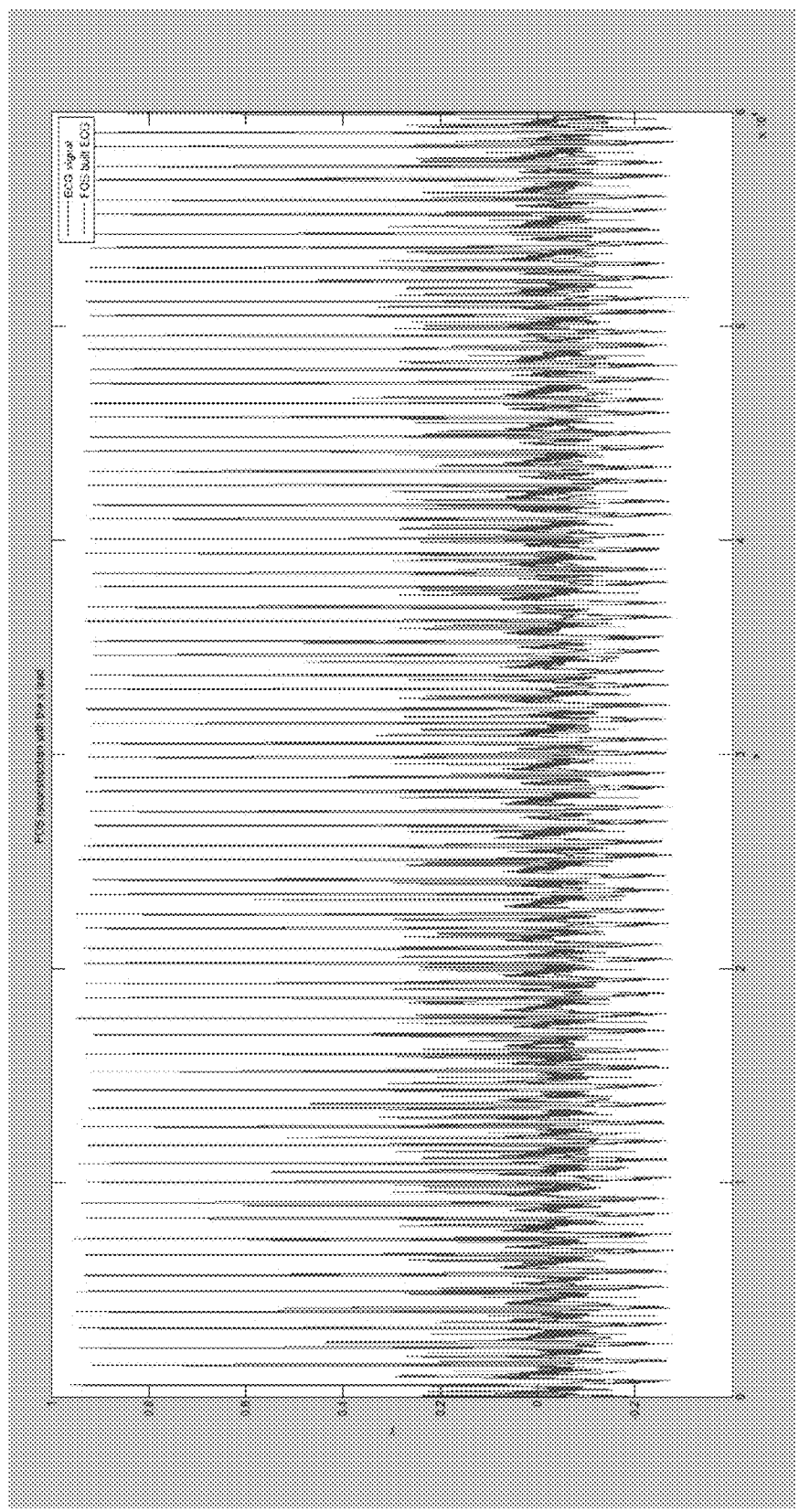
FIG. 21 shows a comparison between FOS reconstructed ECG waveform (red) and a native ECG waveform (blue). The FOS model uses more than 700 nonlinear terms to represent a 60 second ECG. The FOS built signal cannot mimic a 60 second ECG with 700 candidate terms, notice the amplitude and morphology differences between the native and FOS built signals.
Figure 22:
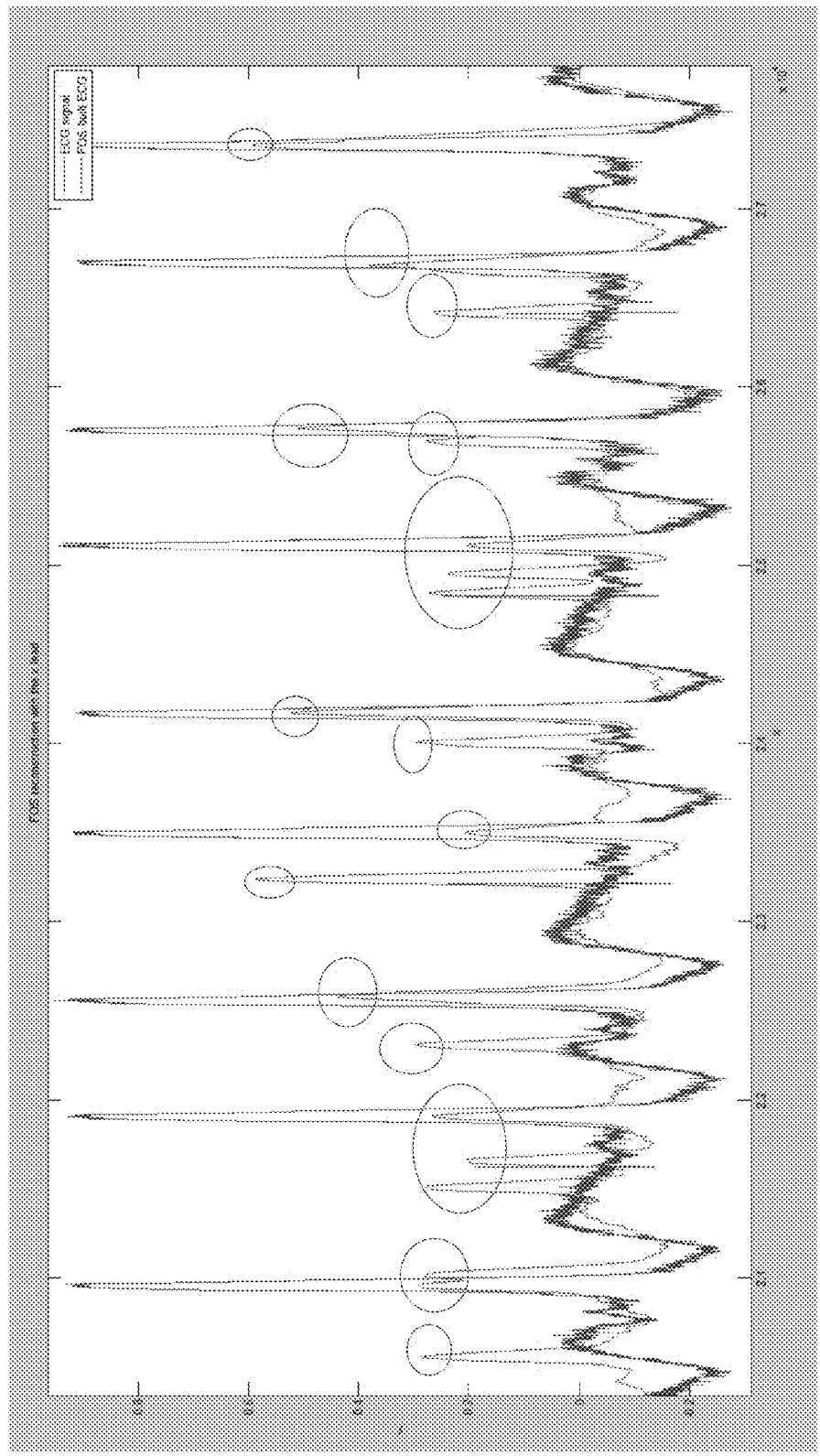
FIG. 22 shows a magnified view comparison between FOS reconstructed ECG waveform (red) and a native ECG waveform (blue). The FOS model uses more than 700 nonlinear terms to represent a 60 second ECG. The FOS built signal cannot rebuild a complex 60 second ECG with 700 or more candidate terms. Amplitude and morphology differences are highlighted with blue circles/ellipses on the FOS built peaks.

The MMP/LARS hybrid process can be used for spectral analysis of very long quasi-periodic biological signals such as, but not limited to, ECG, respiratory function, pulse oximetry, perfusion data, and gamma Electroencephalogram (EEG) signals. The process can be used to create multiple unique 3D Phase Space plots for time series data such as ECG, respiratory rate, pulse oximetry, perfusion data and gamma EEG waves. Traditional model derived methods like fast orthogonal search (FOS) cannot effectively model very long (greater than a 600 seconds) quasi-periodic biological signals since term selection process is based on reducing the overall error of the model maximally with each candidate selection as shown in FIG. 22. This classic forward selection technique, which can be overly greedy, impulsively eliminating covariates candidates which are highly correlated with the biological signal. These errors accumulate on complex signals to make it impossible for classic forward selection technique to use standard static candidate's to mimic a very long time series biological signal as shown in FIG. 21. LARS corrects this problem of making tiny or large hops in the direction of one variable at a time, LARS makes optimally-sized leaps in optimal directions. These directions are chosen to make equal angles (equal correlations) with each of the variables currently in our model. To avoid the problem of fitting noise only the first 80% (by energy) of the signal is fit using LARS and then MMP switches to picking candidates that reduce global mean square error maximally.

Figure 23:
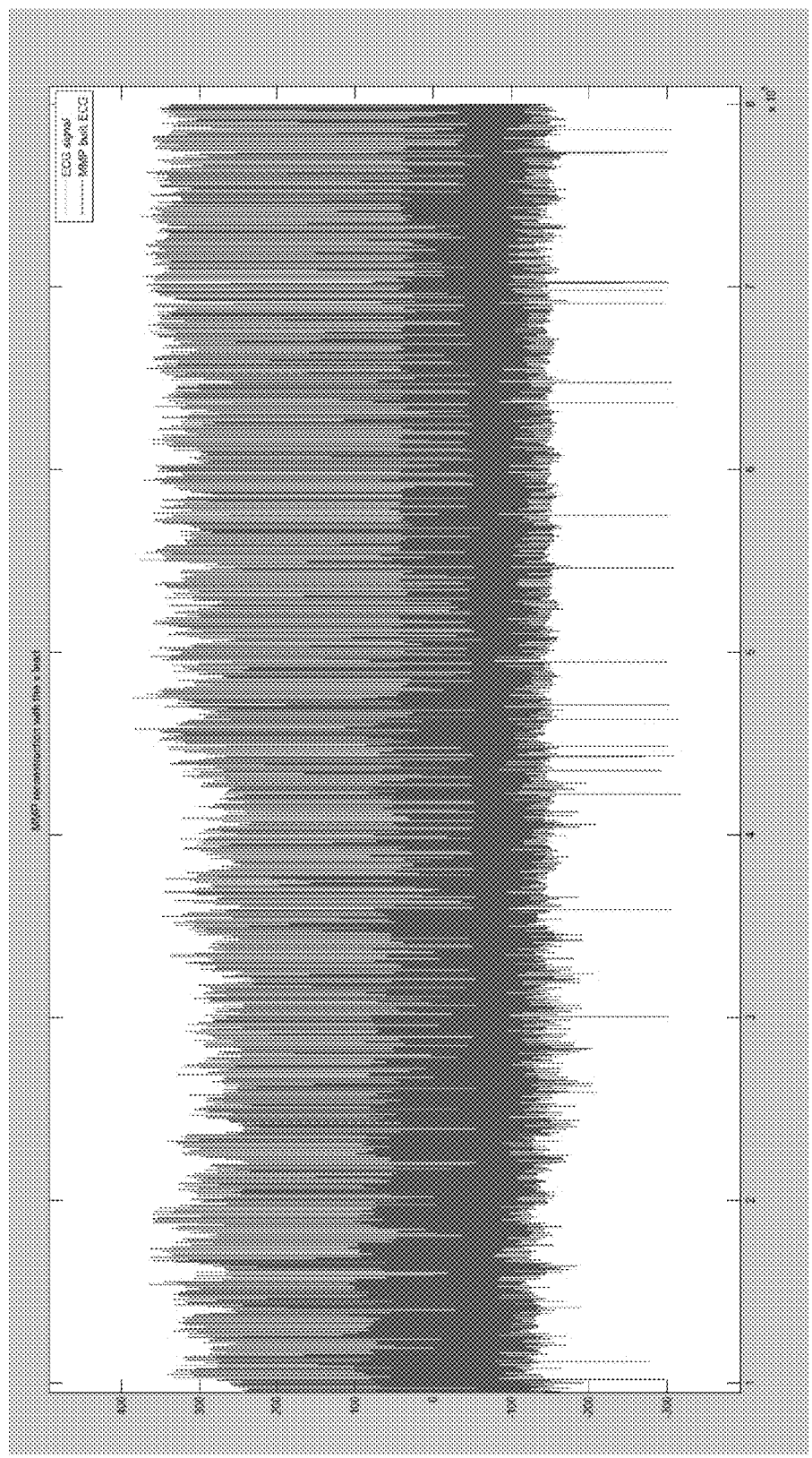
FIG. 23 shows a comparison between MMP reconstructed ECG waveform (red) and a native ECG waveform (blue). The MMP model uses ~700 nonlinear terms to represent an 800 second ECG. The MMP built signal can rebuild a complex 800 second ECG with ~700 candidate terms with a low MSE.
Figure 24:
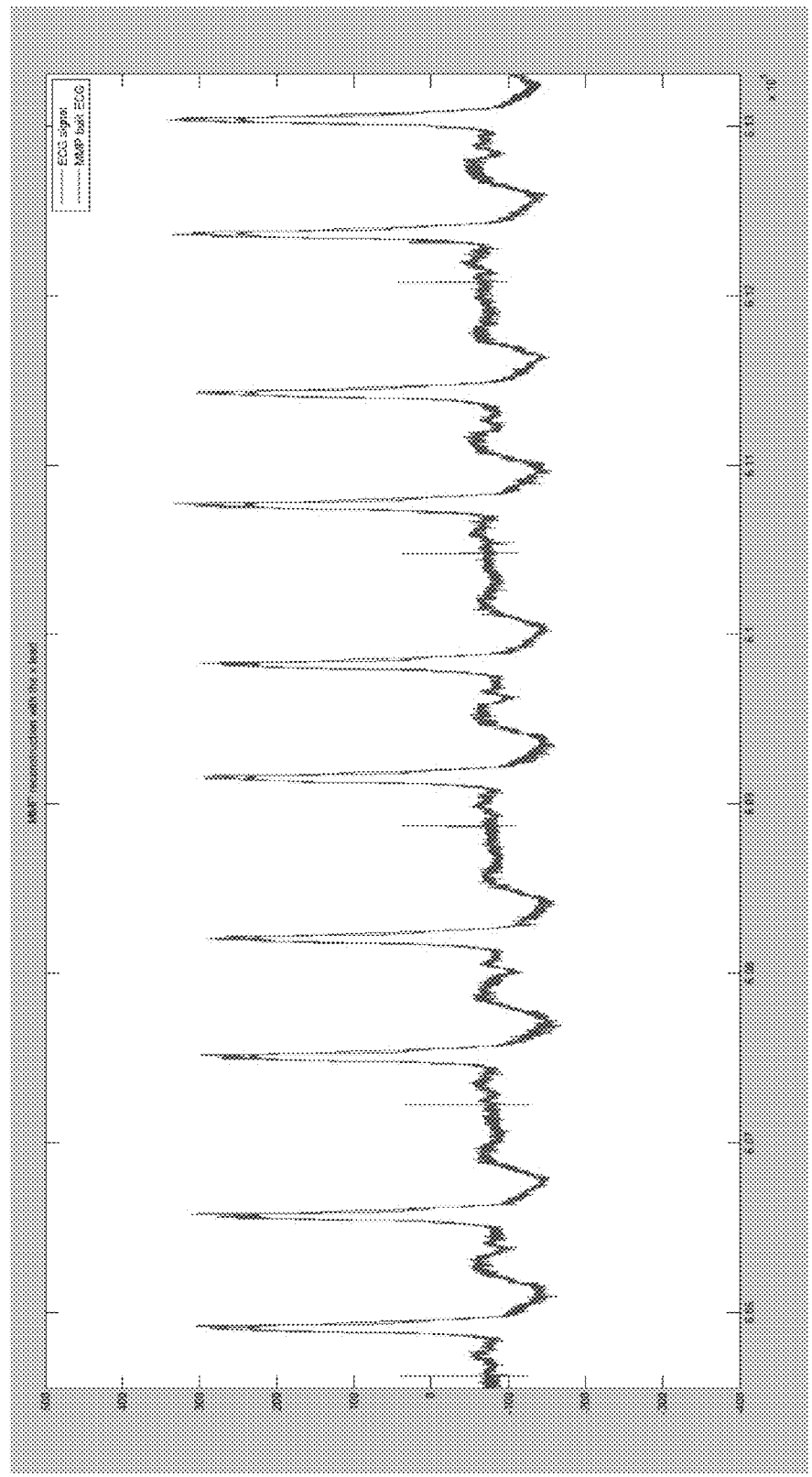
FIG. 24 shows a magnified view comparison between MMP reconstructed ECG waveform (red) and a native ECG waveform (blue). The MMP model uses more than ~700 nonlinear terms to represent an 800 second ECG. The MMP built signal can rebuild a complex 800 second ECG with ~700 candidate terms. Amplitude and morphology differences are minor as the built signal mimics the native ECG signal.

This hybrid MMP/LARS process creates a finite series, or sum, of weighted basis functions. The basis functions can be non-linear mathematical functions, in this case alternating complex exponentials that model the surface ECG as a finite series in which the spectral frequencies are not necessarily integral multiples of a fundamental frequency. The LARS process can generate multiple complex exponential pairs to build an accurate mathematical model of the heart's electrophysiology. The MMP/LARS process can determine the values of the amplitude, frequency and phase of the complex exponentials basis functions by searching through a set of frequencies and calculates the amplitude for each term until there is no significant energy left in the signal. When all the terms are added together it may nearly duplicate the original ECG signal as shown in FIGS. 23 & 24.

The MMP/LARS process creates models with terms that are highly correlated with the target ECG signals. The latest complex exponential pair added to a model has the frequency chosen such that the added pair will cause the greatest reduction in the "most correlated" set LARS then proceeds equi-angularly between i.e. along the "least angle direction (LAD)" and those candidate terms with the lowest mean square error (MSE) of approximating the target ECG signal. The process can continue until there is no complex exponential pair remaining that can cause a reduction in LAD and MSE exceeding a predetermined bottom threshold. The bottom threshold is selected in such a way that unwanted biological signals or 'random noise' that may be present in the ECG signal tend not to be fit by the developed model.

As mentioned previously, FIG. 2 is a flow chart 200 depicting the steps of one embodiment of a modified matching Pursuit (MMP) algorithm which may be used to produce a mathematical reconstruction of the ECG signal according to some of the embodiments disclosed herein. To begin with, at step 202, an ECG signal is received as input. The ECG signal can be represented as a time series for N number of samples in the data set.

At step 204, a functional expansion model to approximate the input ECG time series is created using implicitly created orthogonal functions. The obtained functional expansion includes an implicitly-created orthogonal function with an orthogonal weight B1 and the expansion has a residual error E2. Normally, the implicitly-created orthogonal function is derived from a non-orthogonal candidate function using MMP, based on a least angle orthogonalization process. At 206, MMP chooses a candidate complex exponential pair or other candidate term that causes the greatest reduction of the mean square error (MSE) and estimated parameters are increased in a direction equiangular to each one's correlations with the residual of approximating the input ECG time series. The orthogonal weights B1 are calculated in such a manner that minimizes a mean square error (MSE) and least angle direction (LAD) of the obtained functional expansion from the input ECG time series.

Thereafter at step 208, 210 and 212, the MMP process may be stopped when at least one of the following predefined conditions are met. Firstly, an acceptably small residual LAD & MSE has been achieved. Secondly, the search may also stop when a certain number of terms have been fitted. (This parameter is referred to as maximum terms to add (mTTA)). Thirdly, the search may stop when none of the remaining candidates can yield a sufficient LAD & MSE reduction value. This criterion in such an embodiment would be representative of not having any candidates that would yield an MSE reduction value greater than would be expected if the residual were white Gaussian noise.

At the final step 214, the weights A1 of selected non-orthogonal candidate terms are calculated recursively using orthogonal weights B1. An important part of MMP is that choosing the terms for the model includes the step of searching through one or more sets of candidate terms.

Figure 3:
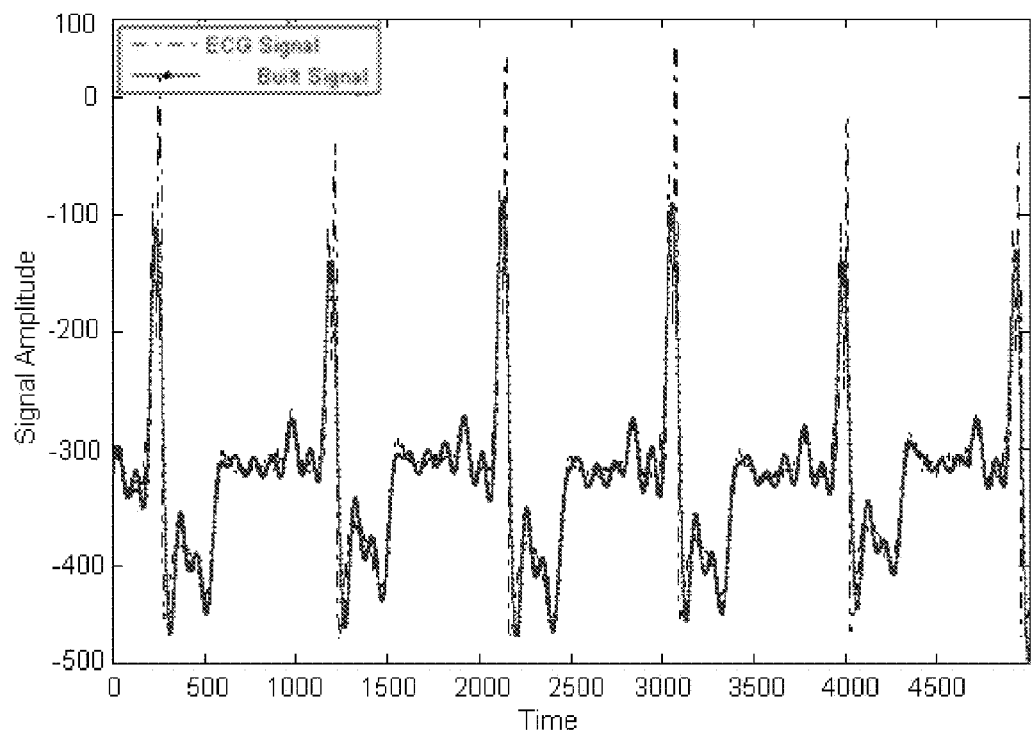
FIG. 3 shows an ECG waveform from patient data vs. a MMP reconstructed ECG waveform using twenty complex exponential pairs of basis functions, for the first 5000 time points in accordance with an embodiment of the present disclosure.
Figure 4:
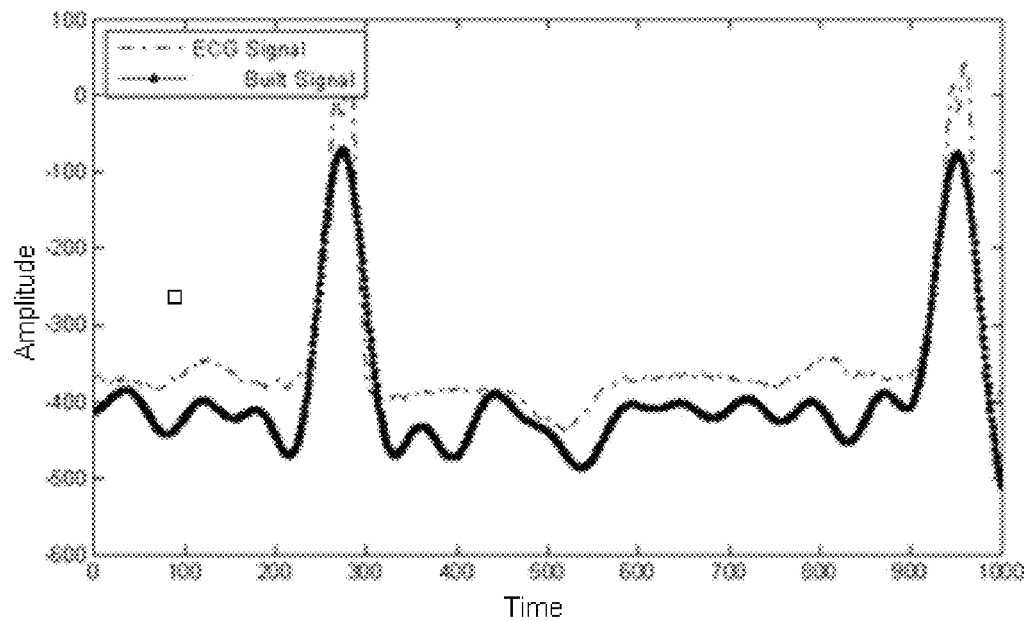
FIG. 4 shows a MMP reconstructed ECG waveform using twenty complex exponential pairs of basis functions, for the first 1000 time points in accordance with an embodiment of the present disclosure.
Figure 5:
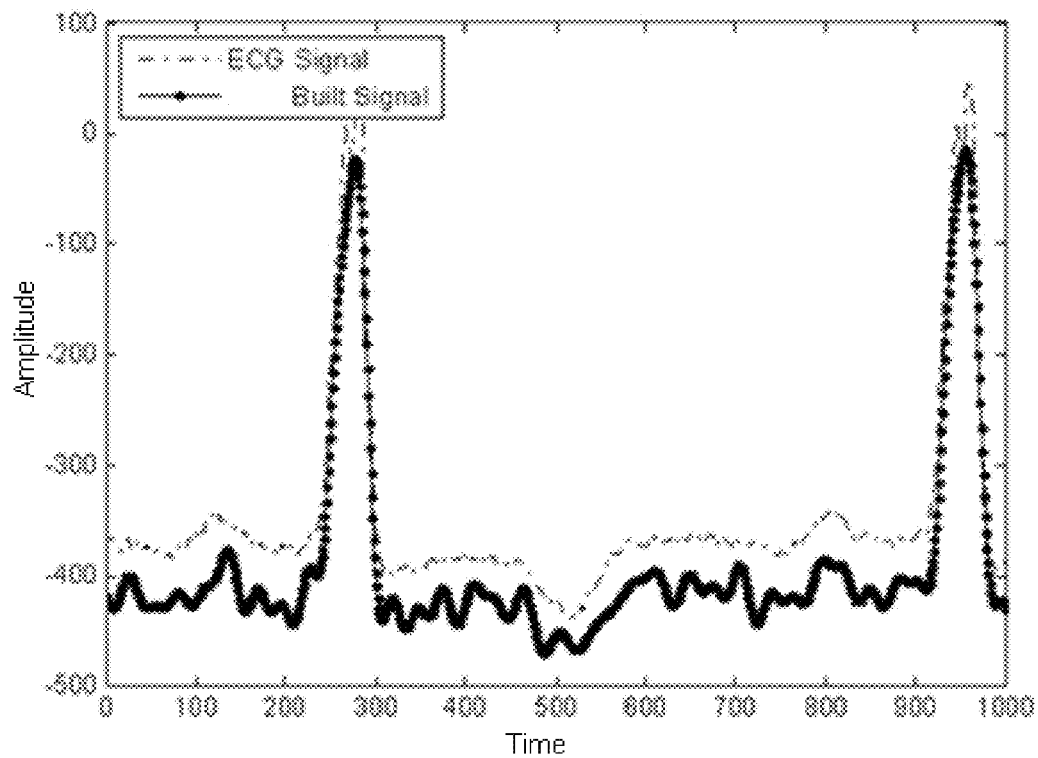
FIG. 5 shows a MMP reconstructed ECG waveform using fifty complex exponential pairs of basis functions in accordance with an embodiment of the present disclosure.
Figure 6:
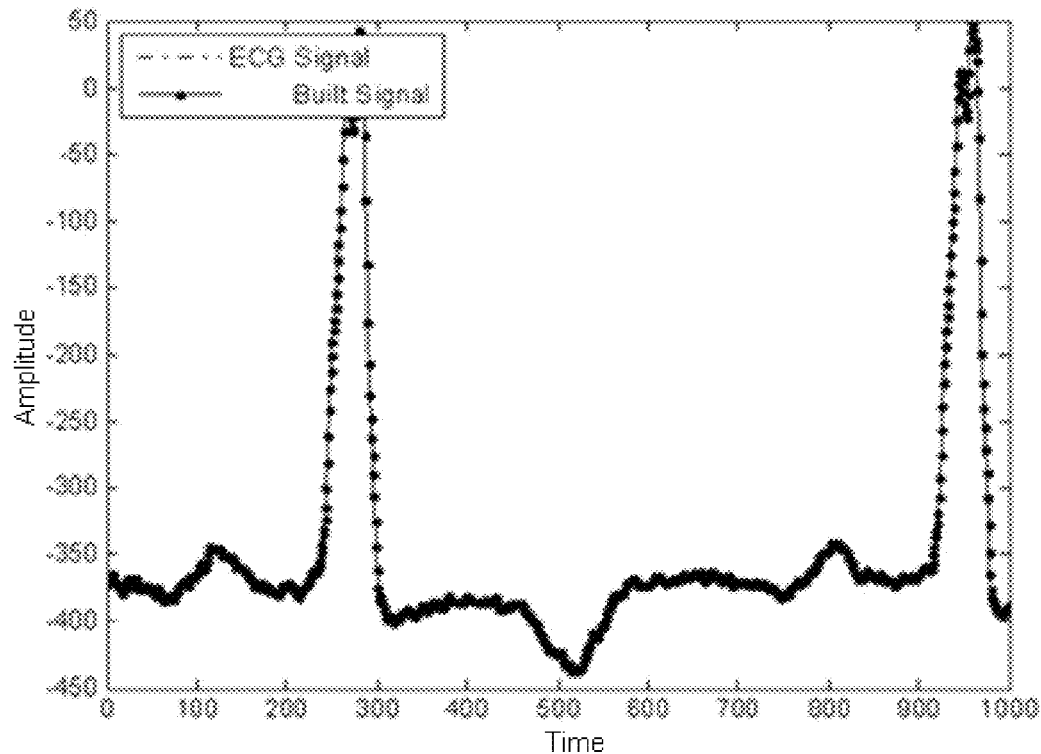
FIG. 6 shows a MMP reconstructed ECG waveform using one hundred complex exponential pairs of basis functions in accordance with an embodiment of the present disclosure.

FIGS. 3-6 show the typical ECG time series data modeled at different resolutions by LARS by changing the maximum number of terms parameter. The addition of sinusoids without enough terms lacks the resolution to model the original signal with high fidelity. A normal MMP reconstructed ECG is shown in FIG. 3. The MMP reconstructed ECG using twenty complex exponentials pairs of basis function terms producing a compression ratio of 33:1 and mean square error of 4.39 is shown in FIG. 4. The LARS reconstructed ECG using fifty complex exponential pairs of basis function terms producing a compression ratio of 13:1 and MSE of 4.38 as shown in FIG. 5. The MMP reconstructed ECG using one hundred complex exponential pairs of basis function terms producing a compression ratio of 10:1, and the MSE reduced to the order of 10-7 is shown in FIG. 6. Thus a higher resolution can be accomplished by using more basis functions.

Figure 7:
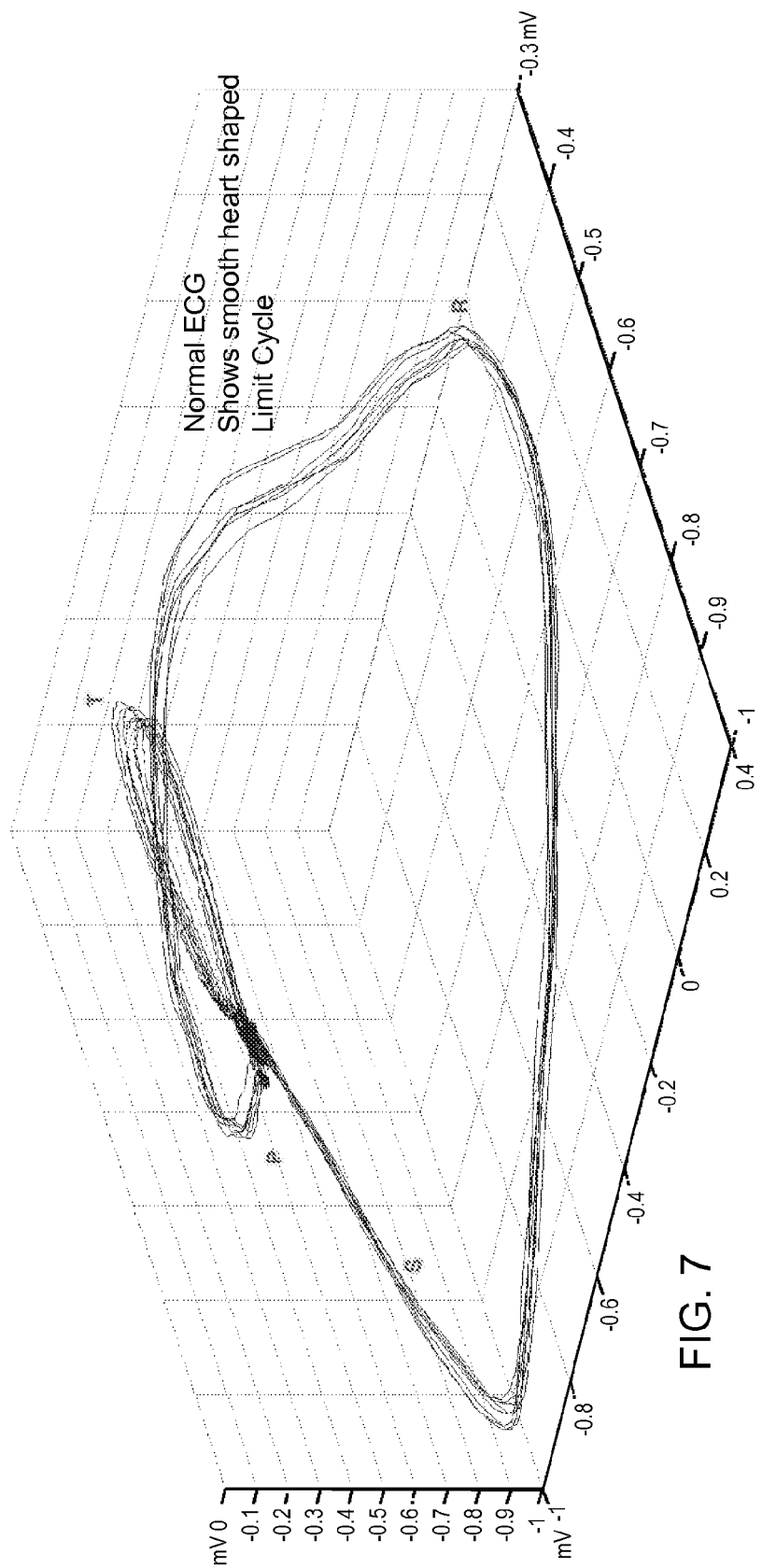
FIG. 7 shows a normalized Phase Space Portrait of an orthogonal lead ECG after applying a Modified Matching Pursuit reconstruction in accordance with an embodiment of the present disclosure.
Figure 19:
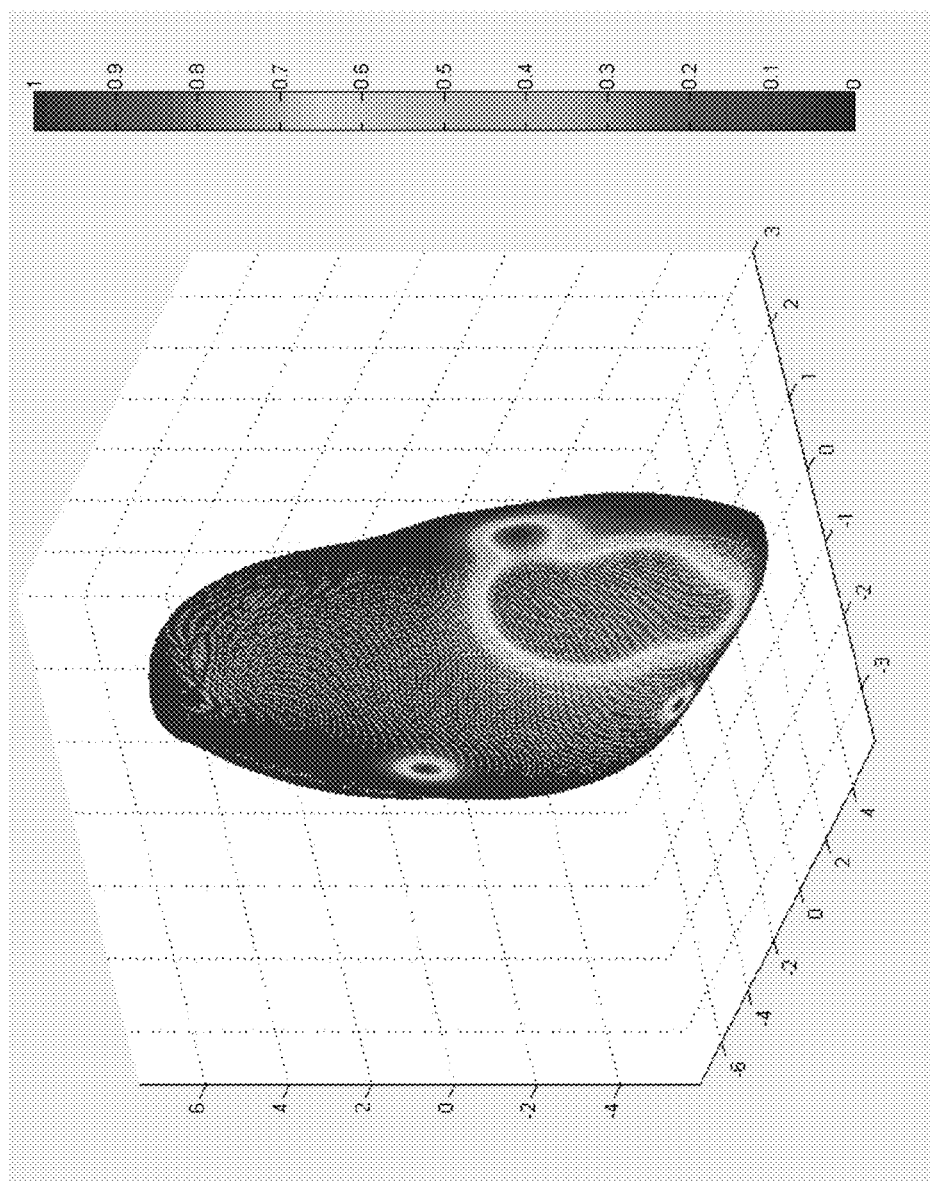
FIG. 19 illustrates an example of a formula generated (blue heart) 3D post MI heart with a lower anterior descending LAD) artery blockage. Ischemic and fibrotic tissue causes wave break-up or CSF and this can be seen as the large red territory which represents the ischemic downstream perfusion bed linked to the LAD occlusion.

FIG. 7 is a phase space plot representing the ECG signal in accordance with an embodiment of the invention. The phase space plot includes a vector space (called a state space or phase space) for the system such that specifying a point in this space specifies the state of the system at a specific time, and vice versa. The dynamics of the system can be interpreted easily now by studying the dynamics of the corresponding phase space points. In theory, dynamic systems are usually defined by a set of ordinary differential equations acting on a phase space. Since the human heart ECG signals can be considered a non-linear dynamic system, therefore to represent ECG signals in the phase space, MMP is used to convert a dynamic system into state space and generate a geometrical phase manifold as shown in FIG. 19. The traditional smooth heart shaped limit cycle of the normal ECG in the form of a P-Q-R-S-T waveform can be seen in FIG. 7. This ECG based manifold can be generated by using the spectral (complex exponential) MMP by reconstructing the signal using the non-linear terms to rebuild and plot the 3D trajectory in phase space which resembles a 3D vector cardiogram.

Figure 8:
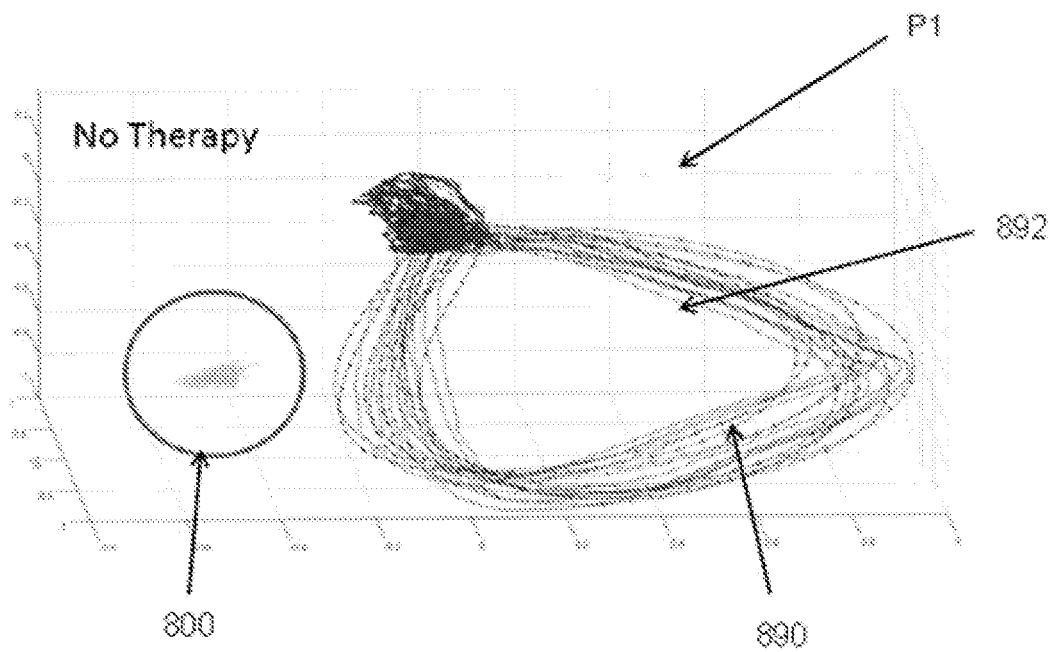
FIG. 8 shows a three-dimensional phase space plot in accordance with an embodiment of the present disclosure representative of a patient's heart without ventricular arrhythmia over a mean three year follow up.
Figure 9:
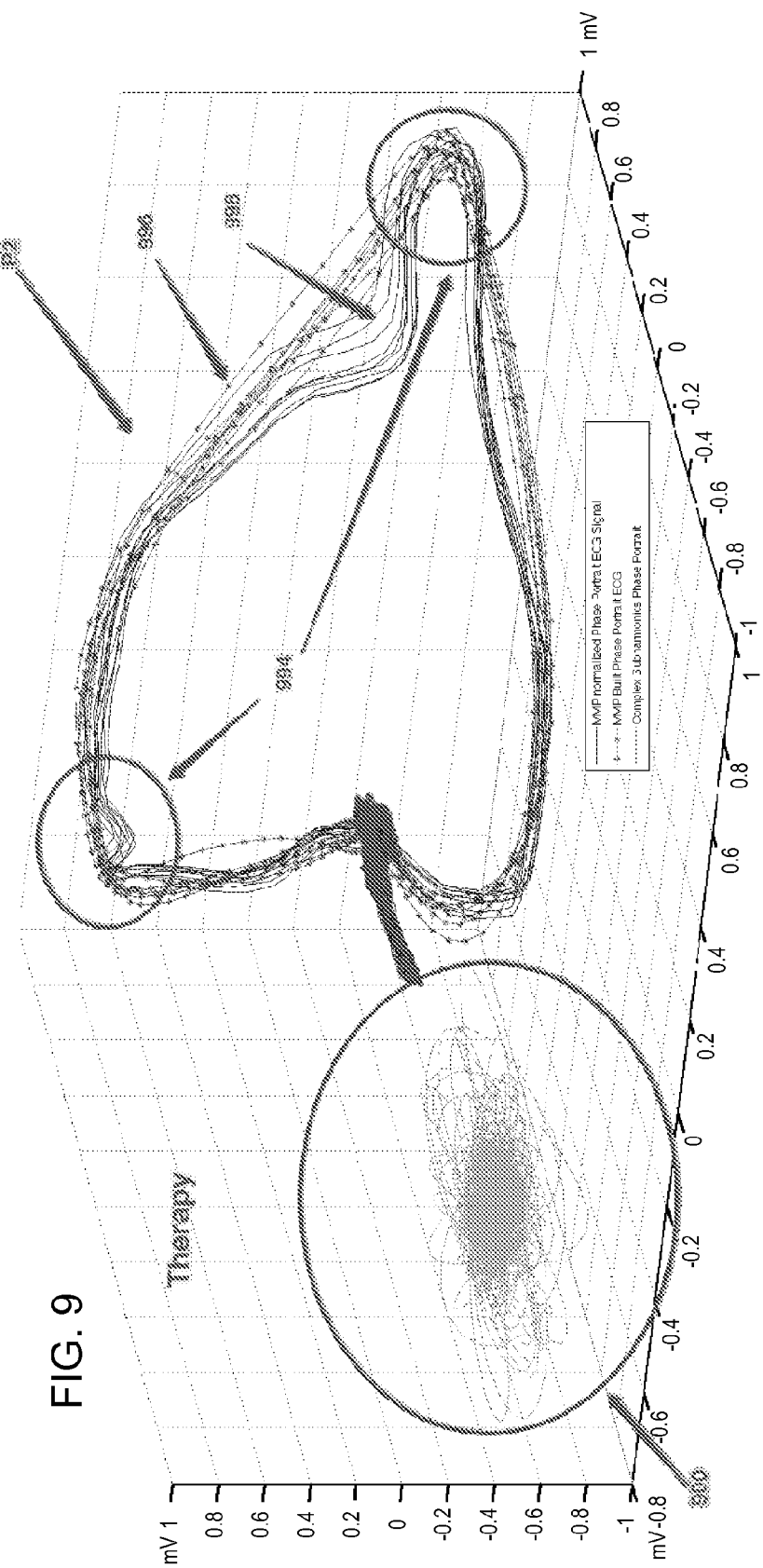
FIG. 9 shows a 3D phase space plot in accordance with an embodiment of the present disclosure representative of a patient's heart with some kind of arrhythmia.

FIGS. 8-9 show the three dimensional (3D) phase space plot of the patient's ECG. FIG. 8 is a representative phase space plot P1 of an implantable cardioverter defibrillator (ICD) recipient without ventricular arrhythmia over a mean three year follow up. The phase space plot P1 includes a plurality of dotted trajectories 890 and a plurality of non-dotted trajectories 892. The dotted trajectories 890 represent a modeled normal conduction path without complex sub-harmonic frequencies (CSF). The non-dotted trajectories 892 represent the actual conduction path of the patient's heart.

FIG. 9 is another phase space plot P2 representative of another patient that received appropriate ICD therapy. The conduction delays 994 can be read from the phase space plots as illustrated for P2. (A similar determination could be made for P1). The departure between the dotted trajectories 996 and the non-dotted trajectories 998 can be interpreted as the conduction delays 994, which may be due to abrupt changes in impedance that are responsible for the generation of complex sub-harmonic frequencies. The intersection of the dotted trajectories 996 and the non-dotted trajectories 998 mark the regions showing conduction delays 994. Although this embodiment uses dotted and non-dotted lines to show the trajectories, other embodiments may use other marking methods to tell the two types of trajectories apart. Other marking methods may include, but are not limited to methods that are discernible from one another in a black and white (monochrome scenario) or methods which color the different trajectories differently.

Circled subspaces 800 and 900 in FIGS. 8 and 9 represents the 3D trajectory magnitude and orientation of complex sub-harmonic frequencies (CSF). The circled subspaces 800 and 900 are the 3D phase space representation of a spectrum of the complex sub-harmonic frequencies. These CSF trajectory subspaces are hidden in the ECG signals. The CSF represents abnormal conduction related to a pathological process in the heart. Normally, low energy components in the output of MMP are associated with the pathological process. There are a variety of pathological processes which can affect the patient's ECG. Such pathological processes can lead to either atrial or ventricular arrhythmias. We subsequently describe the example of MMP analysis assessing ventricular arrhythmia risk: After applying MMP to the ECG, the MMP generates incongruency in the dotted trajectories 996 and the non-dotted trajectories 998. This incongruences or departures can be quantified in the form of the subspaces 800 and 900. Departures between the dotted and non-dotted trajectories represent conduction delays in cardiac impulse propagation. These conduction delays play a role in reentrant excitation since large sudden conduction delays have the potential to spawn spiral and scroll waves which are an important cause of arrhythmias.

Modeling an ECG Signal

To model the ECG signal it is helpful to determine the behavior of the ECG signal. In some embodiments, the Lyapunov exponents can be used to describe the behavior of dynamical systems. Lyapunov exponents tell us the rate of divergence of nearby trajectories, a key component of chaotic dynamics. The Lyapunov exponent measures the average rate of the divergence or convergence of orbits starting from nearby initial points. Therefore, the Lyapunov exponent can be used to analyze the stability of limit cycles and to check for sensitive dependence on initial conditions, that is, the presence of chaotic attractors. This can be done in some embodiments by computing Lyapunov spectra and can be used as a secondary predictor by calculating the change and mean Lyapunov exponent to predict arrhythmias.

A first example method uses a Modified Matching Pursuit (MMP) algorithm to find a noiseless model of the ECG data that is sparse and does not assume periodicity of the signal. A discussion of the MPP algorithm may be found in S. G. Mallat and Z. Zhang, Matching Pursuits with Time-Frequency Dictionaries, IEEE Transactions on Signal Processing, December 1993, pp. 3397-3415, which is incorporated herein by reference in its entirety. This model can be linear combination of certain well behaved signals such as complex exponentials which can be fractionally differentiated as a subspace in parts or as whole series of terms that mimics the system. This contrasts with other procedures where the model output cannot be integrated or fractionally differentiated as a subspace. It should be appreciated that it is not well understood that many physical phenomena are modeled accurately and effectively using fractional derivatives, whereas the classical integer derivative-based models capture these phenomena only approximately. Traditional integer order derivatives depend only on the local behavior of a function, while fractional derivatives depend on the whole history of the function. In the last few decades, considerable focus on fractional calculus has been simulated by the applications of this concept in different areas of physics and engineering. In this embodiment is a method for detecting beat to beat complex sub-harmonic structures in the P wave, T wave and QRS complex of the ECG based on digital differentiation and integration of fractional order. Since these signals are mathematically modeled as a linear combination of the selected atoms, they can be differentiated and integrated of fractional order. Let x'(t), y'(t), and z'(t) be their integer order derivatives respectively, these derivatives and there ratios measure instability only at a local point of the signal and therefore are poor measures of stability for long complex ECG signals with significant beat to beat variability. An alternative to an integer derivative is the use of a fractional calculus to detect abnormal CSF signals in an electrophysiological signal based on its past history. Similarly, in other embodiments, by following the value of the fractional derivative can be determined when the fractional low energy subspace derivative is increasing in amplitude and has the potential to predict reentrant excitation in various locations in the heart.

Figure 18:
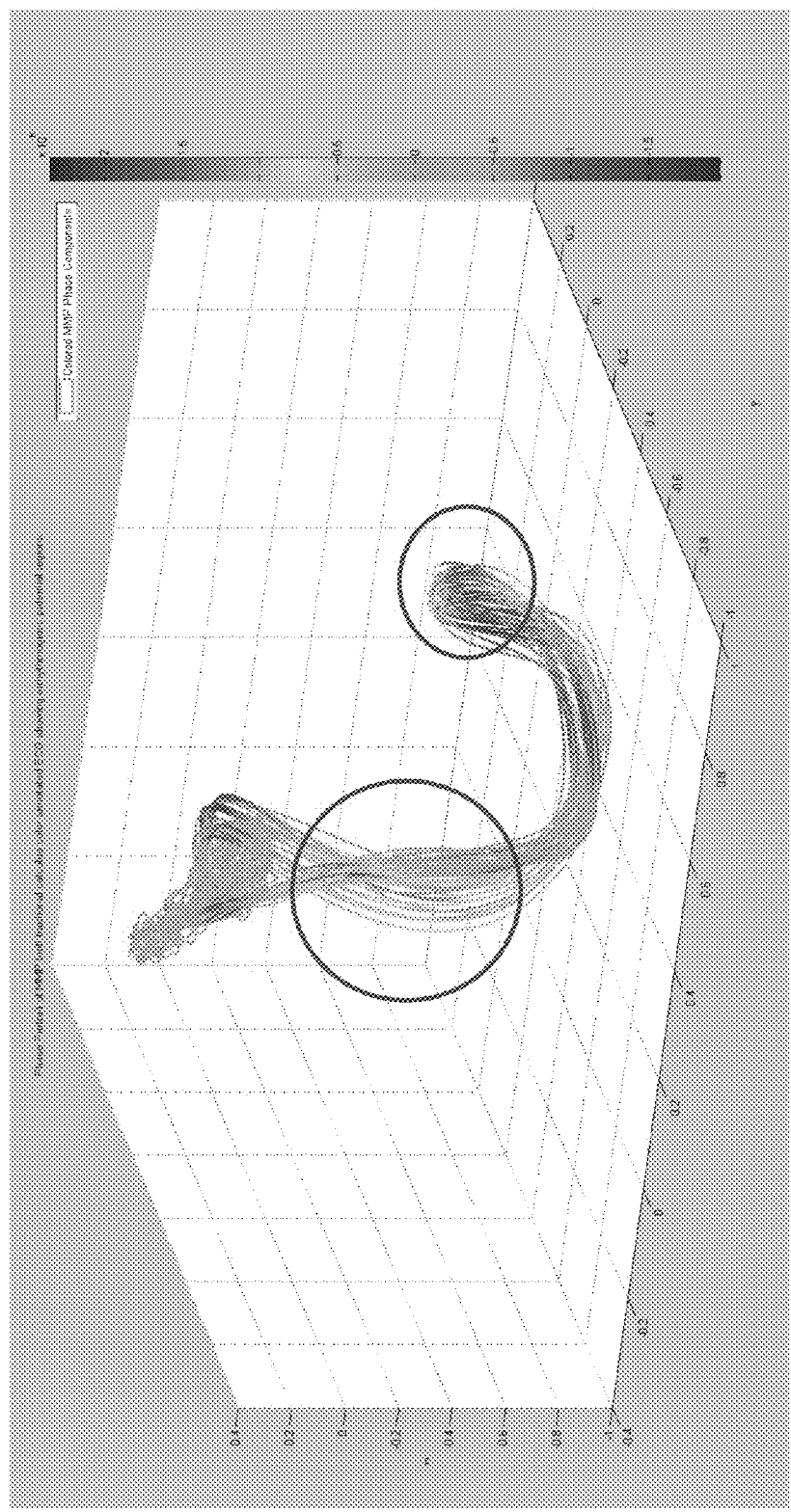
FIG. 18 shows a MMP reconstructed Phase Portrait of a colored ECG vectorcardiogram showing regions of arrhythmogenic potential in red (circled regions)

In some ECG-related embodiments, a color coded scale can be used to indicate the regions of the vectorcardiogram with conduction delays and arrhythmogenic potential. As one non-limiting example, the fractional subspace derivative amplitude can be displayed using a red-blue continuum, where the larger (absolute value) the fractional subspace derivative the more intensely red is the color, and the more negative or smaller the fractional derivative the more intensely blue is the color. The highest positive (absolute value) value of the fractional subspace derivative can be assigned a red color. The smallest (absolute value) or negative value of the fractional derivative can be assigned a blue color. The positive value of the fractional subspace derivative can be considered a region of complex myocardial activation with arrhythmogenic potential. In contrast, smaller value of the fractional subspace derivative can be considered as a region of normal non-reentrant myocardial activation. Every point on the vectrocardiogram represents multiple locations of myocardial activation in the heart of the patient. Thus, the blue and red colors on the vectrocardiogram for such an embodiment could represent the complexity of the depolarization and repolarization of the patient's heart as shown in FIG. 18.

In another embodiment of the present disclosure, formula models can be built using genetic algorithms and MMP models whereby the pathological event identified is a prediction of a clinical outcome or diagnosis, e.g. sudden cardiac death, atrial or ventricular fibrillation, death/survival. Genetic algorithm (GA) is a search heuristic that mimics the process of natural evolution. This heuristic is routinely used to generate useful solutions to optimization and search problems. Genetic algorithms use the principles of inheritance, mutation, selection, crossover and evolution to produce several solutions to a given problem. For embodiments examining ECG signals, the non-linear functions can be selected using genetic operators to find the best functions to be selected from candidate terms which contain variables of metrics like cardiac function, the QT interval, heart rate, conduction delays, ejection fraction, other measures of cardiac function, and vector product thereof. These ideal functions, chosen from a pool of functions like sin, cos, cos h, sin h, tan h, Gaussian functions, and logistic functions, can be selected using a GA and optimized using MMP. Depending on the significance of best non-linear terms, there may be thousands or tens of millions of candidate terms, but GA and MMP model can build a concise correlated model with unobvious terms that can be linked to indicators of clinical outcome or diagnosis. This approach enables using many different previously proposed indicators of cardiac function together and making new predictors by GA and MMP-selected combinations of existing indicators.

It should be appreciated that the stability of the system can also be checked using the Lyapunov exponent in desired embodiments. However, the Lyapunov exponent can be calculated without using the output from the MMP model.

The Lyapunov exponent can be calculated as the rate of separation between beat to beat limit cycle trajectories so it can be a spectrum of exponents which can be calculated on long quasi-periodic records.

According to an embodiment of the disclosure, the Lyapunov exponent can be calculated separately for the ventricles and the atrium. For the ventricle, the QRS wave of the ECG signal is detected and various points the average is calculated. Once the average is calculated, a baseline reference can be calculated. Whenever the Lyapunov exponent goes above the baseline reference, it will indicate the relative stability of the system. In other words, it indicates that particular region of the ventricles is fine. Similarly for atrium, the P wave is detected in the system and the Lyapunov exponent is calculated for P wave. In the next step, the average is measured and checked for relative change in stability. This can be evaluated to the entire limit cycle. Every point on the limit cycle can have hundreds Lyapunov exponents and within each point while moving along the limit cycle, it can be checked whether the system is moving towards stability or instability. Large positive values of Lyapunov exponents indicate the presence of a strange attractor which is linked to anisotropic conduction which is a cause of arrhythmias.

The low energy terms can be sorted and selected by amplitude components. In one illustrative embodiment, the last 20% of the terms can be chosen can be taken as the low energy terms. Other embodiments may use higher or lower percentages of the terms as the low energy terms. These chosen last few terms should be picked to contain a lot of the hidden low energy signal dynamics. We can find the fractional subspace derivative of these components, since it is a linear combination of complex exponentials.

Figure 20:
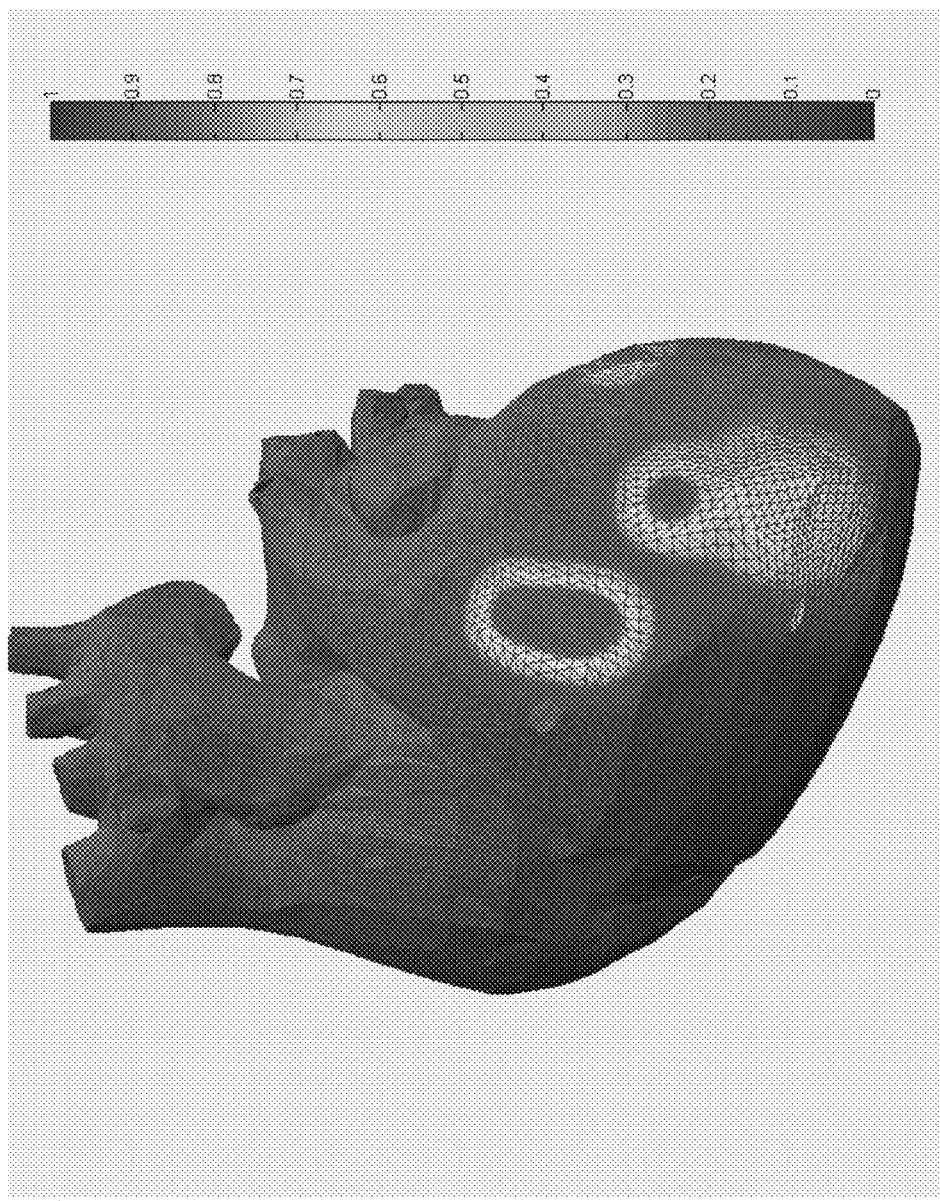
FIG. 20 illustrates an example of 3D vector annotated post MI heart with a lower anterior descending LAD) artery blockage. Ischemic and fibrotic tissue causes wave break-up or CSF and this can be seen as the large red territory which represents the ischemic downstream perfusion bed linked to the LAD occlusion.

According to an embodiment of the disclosure, the method can also be used to build the three dimensional (3D) model of the heart. This method involves preparing a 3D phase space diagram using the ECG and superimposing the 3D phase space diagram on a 3D outline of a heart so that we can show where the damaged area is present on or within the heart. It should be appreciated that the heart can be cut and sliced to show the various regions to provide a three dimensional mesh of the whole heart as shown in FIG. 20. This is digital reconstruction of the ECG of the heart showing Epicardium, Endocaridum and all this based on a three orthogonal lead ECG. The traditional method uses a combination of CT scan, and approximately two hundred electrodes from top to bottom. They register a frame and use electrodes to generate a voltage gradient map. The present disclosure makes use of only three electrodes and provides details of the heart non-invasively. Thus, it is inexpensive.

It is always helpful for a doctor to detect myocardial pathology. The current method generates the 3D model of the heart with high speed by using the intrinsic electrical signals generated by the heart. The traditional method uses Magnetic resonance imaging (MRI) or Computed Tomography (CT) for the diagnostic imaging of the heart to analyze the pathological structures in the heart. The MRI uses a contrast agent to enable the user to view the contrast image of the cardiac scar tissue within the heart. The scar or hypoxic myocardial tissue will absorb more contrast agent, which will identify the regions of the abnormal cardiac tissue. If there are multiple regions with abnormal conduction, then it is not possible to determine which region specifically is causing arrhythmogenesis in the heart using MRI. MRI cannot determine the arrhythmogenic potential of the patient's heart. In contrast, the current method uses the intrinsic electrical conduction of the heart to generate a 3D model of the heart. Thus, it helps in determining the location of the cardiac tissue with arrhythmogenic potential. Ischemic heart disease, or myocardial ischemia, is a disease characterized by reduced blood supply of the heart muscle, usually due to coronary artery disease. Significant ischemic heart disease will alter the three dimensional conduction properties of the myocardium in the perfusion bed downstream of the coronary artery occlusion permanently which can be detected in a resting high resolution ECG. These low energy signal dynamics can be detected and localized using a fractional subspace derivative.

It should be appreciated that the twelve lead ECG can be transformed in to the three lead vectrocardiogram (VCG) or vice versa using a MMP derived transform. To identify such models, training data can be used where both the twelve lead ECG and the three lead VCG have been simultaneously recorded. Then MMP models can be identified when the twelve lead ECG signals are the training inputs and the three lead VCG signals are the desired outputs, resulting in models that can transform twelve lead ECG into approximately three lead VCG. Alternatively, MMP models can be identified when the three lead VCG signals are the training inputs and the twelve lead ECG signals are the desired outputs, resulting in models that can transform three lead VCG into approximately twelve lead ECG. The VCG uses 3 channels connected in an orthogonal lead arrangement. It should also be appreciated that the transform of twelve-lead ECG signal to three-lead vectorcardiography or a reverse transform of three-lead vectorcardiography to twelve-lead ECG can be done by using MMP. Traditionally, the methods use processes like Karhunen-Loeve, Dower, and Levkov to convert the VCG to ECG and vice versa. MMP based transformation provides efficient compression, white noise removal, and removal of baseline drift with conversion of ECG into a vectrocardiogram, or vice versa.

According to another embodiment of the invention, the MMP process can also be used for the purposes of a stress test since this form of testing is a well-established means of detecting underlying ischemic heart disease. The patient will have their heart rate increased (i.e. stressed) by either exercise or pharmaceutically. In some embodiments, the methods disclosed herein may also be used to identify underlying ischemic heart disease without the need to put the patient under stress conditions, thereby avoiding putting such patients at higher risk with a stress test. As with the previous methodology, a high resolution ECG will be obtained at increasing heart rates including peak heart rate. These data will then be assessed as per the previously described methodology.

According to yet another embodiment of the disclosure, the MMP generated subspaces can also be used to extract the fetal ECG from an ECG recorded on the mother's abdomen. The process for extracting the fetal ECG consists of two steps: first, the ECG of the fetus is extracted from the original signal using a 3D MMP transform. Maternal ECG represents the remaining subspace energy.

According to still another embodiment of the disclosure, the MMP process can also be used to calculate the heart rate variability. The brain is linked to the autonomic nervous system which, amongst many systems in the body, controls heart rate and cardiac output. Heart rate variability analysis traditionally requires observing variability of the R-R interval. Modified matching pursuit (MMP) can be used to model a very long (hundreds of seconds) multi-lead ECG signal. The 3D ECG data can be used to generate other subspaces of the ECG signals which can replace traditional variability analysis. These subspaces are linked to specific properties of non-linear cascades terms and as such can be used to model the states of the brain and the heart. More specifically, this invention is a method and associated apparatus for evaluating electrophysiological signals in a manner that will sensitively and specifically predict current and future pathological events such as heart disease, diabetic autonomic neuropathy, cardiac arrhythmias, Parkinson's disease, epilepsy, brain injury/disorders and altered states of cognition such as bipolar disorder and attention deficit disorder (ADD).

According to still another embodiment of the invention, the method is also used as a tool to track severity of illness in critically ill patients in the ICU (Intensive Care Unit). The combination of MMP and 3D phase space plot offers a potential opportunity to quantify severity of illness, thereby determining if patients are improving or deteriorating during a longer period of time. The MMP process produces a multidimensional formula for the ECG time series of any given length. This formula describes a dynamic system given by a set of real numbers (a vector) which can be represented by a point in an appropriate phase space. Small changes in the state of the system correspond to small changes in the set of real numbers such that a point in space becomes a point in time in the 3D ECG signal. For a given time interval only one future state follows from the current state. This is the dynamic systems approach which is used to generate the differential equations that model the dynamic system of the heart. This dynamic model has the potential to model the heart's stability at different heart rates and to simulate the effectiveness of cardio-active medications. This method allows for accurate prediction of arrhythmias (Atrial Fibrillation/Ventricular Fibrillation/Ventricular Tachycardia) that may lead to sudden cardiac death of the patient.

In other aspects of this particular invention, the biological noise during inhalation and exhalation, and external noise from communication devices, switching power supplies and terrestrial power lines, can be detected and excluded or attenuated by customizing terms generated by MMP.

Figure 10A:
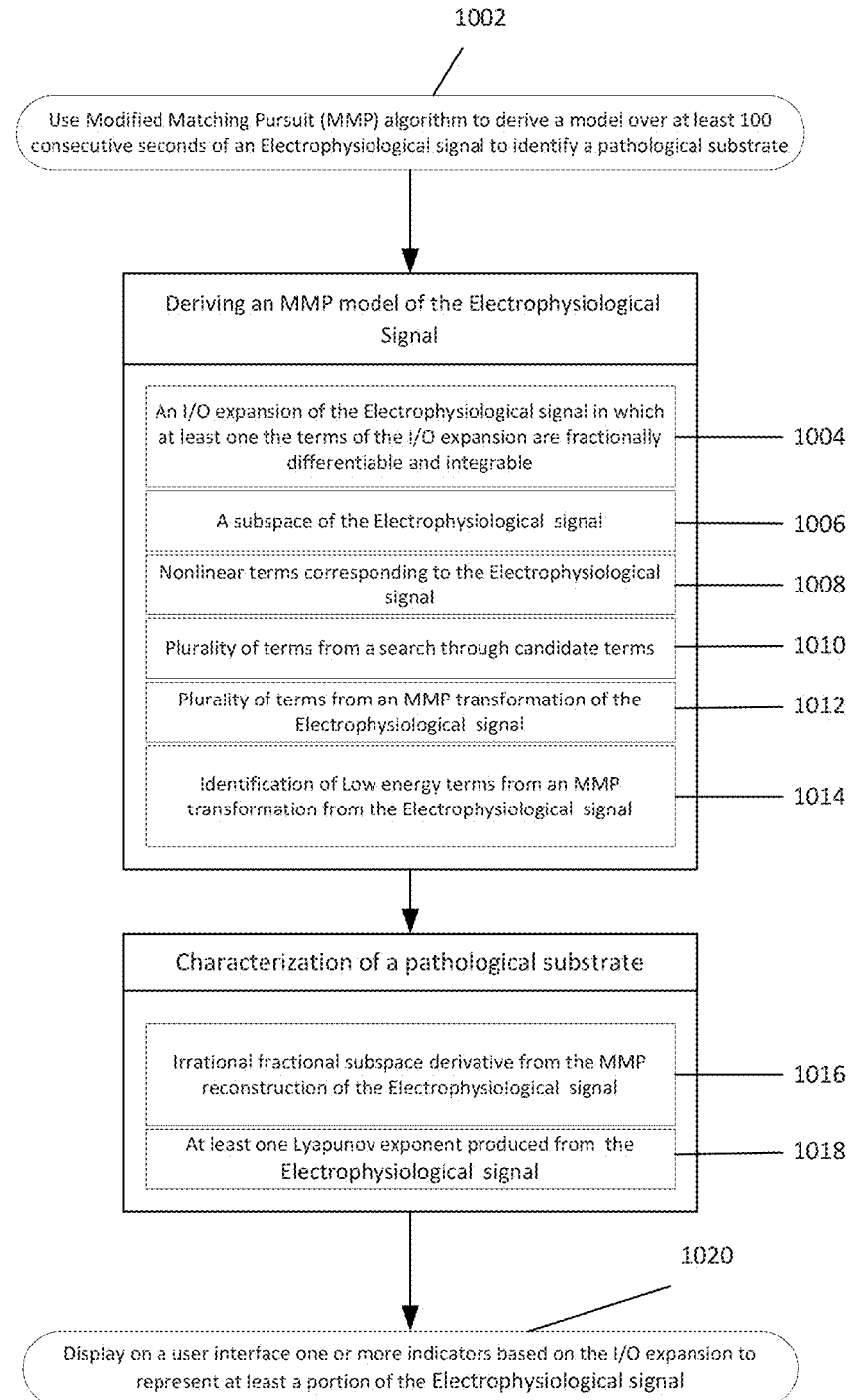
FIGS. 10A-10B illustrate methods for evaluating an electrophysiological signal.

FIG. 10A illustrates an example method for evaluating an electrophysiological signal. In FIG. 10A, a mathematical reconstruction over at least one cycle of the electrophysiological signal (1002) is used to identify a pathological event. Examples of electrophysiological signals include, but are not limited to an electrocardiogram (ECG), an electroencephalogram (EEG), a gamma synchrony signal; a respiratory function signal; a pulse oximetry signal; a perfusion data signal; a quasi-periodic biological signal; a fetal ECG; a blood pressure signal; and a heart rate signal. Examples of a pathological event which may be identified include, but are not limited to a heart disease, a cardiac arrhythmia, a diabetic autonomic neuropathy, Parkinson's disease, a form of epilepsy, a brain injury, an altered state of cognition, a stability of a heart at different heart rates, an effectiveness of a medication, an ischemic, a silent ischemia, an atrial fibrillation, a ventricular fibrillation, a ventricular tachycardia, a blood vessel block, and attention deficit disorder.

The mathematical reconstruction of the electrophysiological signal may comprise various elements, depending on the embodiment. For example, in some embodiments (1004), the mathematical reconstruction of the electrophysiological signal comprises an input/output (I/O) expansion of the electrophysiological signal, in which at least one of the terms of the I/O expansion are fractionally differentiable. In some embodiments, at least one term of the I/O expansion that is analytically fractionally differentiable. In other embodiments, the I/O expansion may comprise a fractional integral of the mathematical reconstruction. In still further embodiments, the I/O expansion may comprise a fractional derivative of the mathematical reconstruction of the electrophysiological signal to the mathematical reconstruction of the electrophysiological signal. In still other embodiments, the I/O expansion may comprise irrational fractional subspace derivative of the mathematical reconstruction of the electrophysiological signal (1016).

There are a couple of points about the low-energy component subspace (made from the last, e.g., 20% terms found by MMP) that are interesting and useful. First, the fractional integral and derivative of these components can be noiselessly determined, since it is a linear combination of selected candidate terms, and this fractional derivative can be useful to distinguish ventricular tachycardia potential in post myocardial infarction patients and those with congenital heart defects. In addition, there are some useful fractional properties to consider. Thus suppose that x(t), y(t), and z(t) are respectively the X, Y, and Z coordinates of the low-energy component and let $x^\alpha(t)$, $y^\alpha(t)$, and $z_\alpha(t)$ be their irrational fractional derivative of order α that can be any real (or complex) number. Then, the magnitude of these irrational fractional derivatives can indicate instability when large and positive. Consider the regions when the irrational fractional derivatives are positive, in such regions, the low energy reentrant wavelets have the potential to be arrhythmogenic.

In other embodiments, the mathematical reconstruction of the electrophysiological signal may comprise a subspace of the electrophysiological signal (1006). The subspace of the electrophysiological signal may be selected to remove one or more complex subharmonic frequencies from the electrophysiological signal.

In other embodiments, the mathematical reconstruction of the electrophysiological signal may comprise non-linear terms corresponding to the electrophysiological signal (1008). In further embodiments, the mathematical reconstruction of the electrophysiological signal may comprise a plurality of terms from a search through candidate terms (1010). In still other embodiments, the mathematical reconstruction of the electrophysiological signal may comprise a plurality of terms from a modified matching pursuit (MMP) transformation of the electrophysiological signal (1012). For other embodiments, the mathematical reconstruction of the electrophysiological signal may comprise a plurality of terms from a MMP transformation of low energy terms produced from the electrophysiological signal (1014). In some embodiments, the method for evaluating an electrophysiological signal may also include a step (1020) of displaying on a user interface one or more indicators based on the input/output (I/O) expansion to represent at least a portion of the electrophysiological signal. For embodiments which have a mathematical reconstruction which is not based on an I/O expansion, the user interface may be used to display one or more indicators based on the mathematical reconstruction of the electrophysiological signal.

In some embodiments, the one or more indicators may be displayed on a phase space plot. In other embodiments, the one or more indicators may be displayed on at least a portion of the electrophysiological signal. In still other embodiments, the one or more indicators may be highlighted to further convey information about the pathological substrate identified from the mathematical reconstruction of the electrophysiological signal. The highlighted indicators may comprise color coded indicators, shaded indicators, one or more type of broken lines, and/or one or more type of line thicknesses.

In some embodiments, the one or more indicators may be displayed on a physiological image corresponding to the electrophysiological signal. Depending on the embodiment, the electrophysiological signal may comprise an electrocardiogram (ECG) and the physiological image may comprise an image of at least a portion of a heart and/or at least a portion of myocardial architecture. In other embodiments, the electrophysiological signal may comprise an electroencephalogram (EEG) and the physiological image may comprise an image of electrical patterns in a portion of a brain.

In further embodiments, the physiological image may comprise a two-dimensional image, a three-dimensional image, a time changing image (for example, a video, or time lapsed set of images at equal or non-equal intervals), an impedance based tissue model, or a tissue architecture from an actual subject from whom the intrinsic electrophysiological signal was obtained.

Figure 10B:
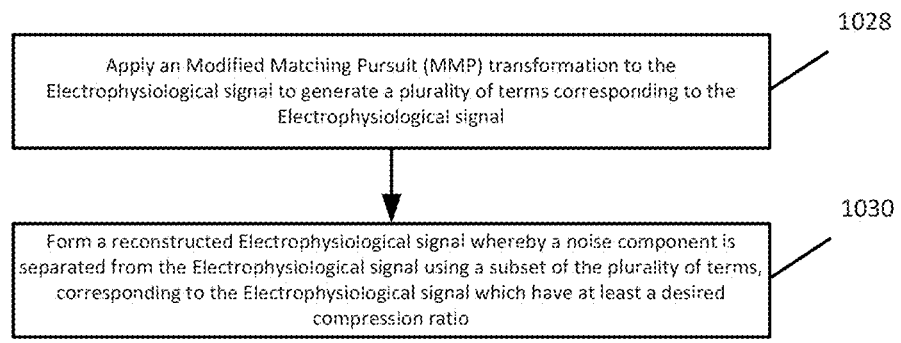

FIG. 10B illustrates another embodiment of a method of evaluating an electophysiological signal. A MMP transform is applied 1028 to the electrophysiological signal to generate a plurality of terms corresponding to the electrophysiological signal to generate a plurality of terms corresponding to the electrophysiological signal. A reconstructed electrophysiological signal is formed 1030 whereby a noise component is separated from the electrophysiological signal using a subset of the plurality of terms, corresponding to the electrophysiological signal, which have at least a desired compression ratio. In some embodiments, a desired compression ratio is about 30 to 1, however higher or lower compression ratios may be desirable in other embodiments.

In further embodiments, the electrophysiological signal may comprise an electrocardiogram (ECG) signal, and the method may further comprise transforming the ECG signal into a vectrocardiogram. In other embodiments, the electrophysiological signal may comprise an electrocardiogram (ECG) signal from a mother's abdomen, and the method may further comprise extracting a fetus ECG from the mother's abdomen ECG using a selective subspace MMP transformation.

Figure 11:
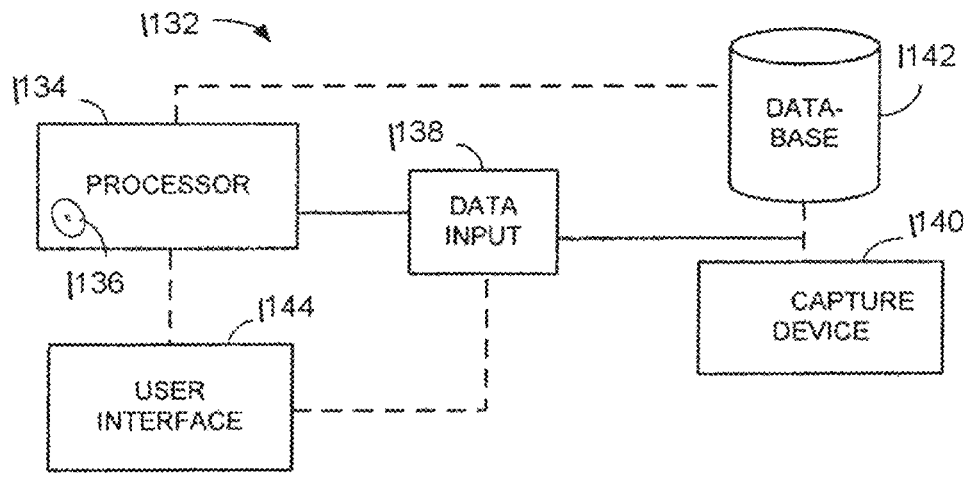
FIGS. 11-14 schematically illustrate different embodiments of a system for evaluating an electrophysiological signal.

FIG. 11 schematically illustrates an embodiment of a system 1132 for evaluation of an electrophysiological signal. The system 1132 has a processor 1134 which is configured to identify a pathological event from a mathematical reconstruction of the electrophysiological signal. Embodiments of suitable processes and method steps to make this identification have already been discussed above. The processor 1134 may be a computer executing machine readable instructions which are stored on a non-transitory computer readable medium 1136, such as, but not limited to a CD, a magnetic tape, an optical drive, a DVD, a hard drive, a flash drive, a memory card, a memory chip, or any other non-transitory computer readable medium. The processor 1134 may alternatively or additionally include a laptop, a microprocessor, an application-specific integrated circuit (ASIC), programmable logic array, digital circuitry, analog circuitry, or any combination and/or plurality thereof. The processor 1134 may be a stand-alone unit, or it may be a distributed set of devices.

A data input 1138 is coupled to the processor 1134 and configured to provide the processor 1134 with the electrophysiological signal. An electrophysiological signal capture device 1140 may optionally be coupled to the data input 1138 to enable the live capture of the electrophysiological signal. Examples of electrophysiological signal capture devices include, but are not limited to an electrocardiogram Holter monitor; a twelve lead electrocardiogram monitor; an eight lead electrocardiogram monitor; an electrocardiogram monitor using a bipolar lead system, an electrocardiogram monitor using a unipolar lead system, intracardiac signals, a brain computer interface (BCI), a mind machine interface (MMI), a direct neural interface, a brain machine interface, a perfusion blood oxygenation sensor, a blood pressure sensor, a breathing rate sensor, and a fetal electrocardiogram monitor. Similarly, a database 1142 may optionally be coupled to the data input 1138 to provide a previously captured electrophysiological signal to the processor 1134. Database 1142 can be as simple as a memory device holding raw data or formatted files, or database 1142 can be a complex relational database. Depending on the embodiment, none, one, or multiple databases 1142 and/or electrophysiological signal capture devices 1140 may be coupled to the data input 1138. The electrophysiological signal capture device 1140 may be coupled to the data input 1138 by a wired connection, an optical connection, or by a wireless connection. Suitable examples of wireless connections may include, but are not limited to, RF connections such as Near field communication (NFC) or using an 802.11x protocol or the Bluetooth® protocol. The electrophysiological signal capture device 1140 may be configured to transmit data to the data input 1138 only during times which do not interfere with data measurement times of the electrophysiological signal capture device 1140. If interference between wireless transmission and the measurements being taken is not an issue, then transmission can occur at any desired time. Furthermore, in embodiments having a database 1142, the processor 1134 may be coupled to the database 1142 for storing results or accessing data by bypassing the data input 1138.

The system 1132 also has a user interface 1144 which may be coupled to either the processor 1134 and/or the data input 1138. The user interface 1144 can be configured to display the one or more indicators discussed above. The user interface 1144 may also be configured to allow a user to select electrophysiological signal data from a database 1142 coupled to the data input 1138, or to start and stop collecting data from an electrophysiological signal capture device 1140 which is coupled to the data input 1138.

Figure 12:
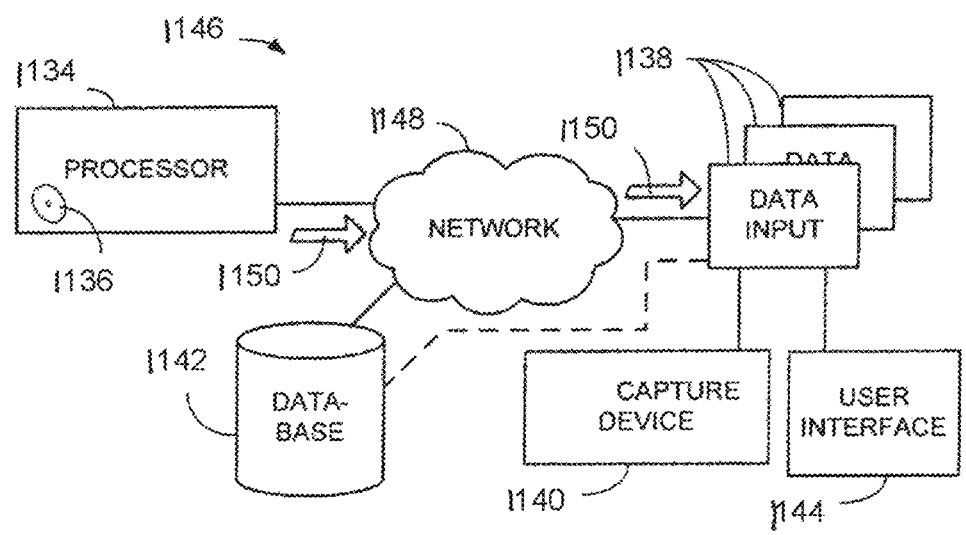
Figure 13:
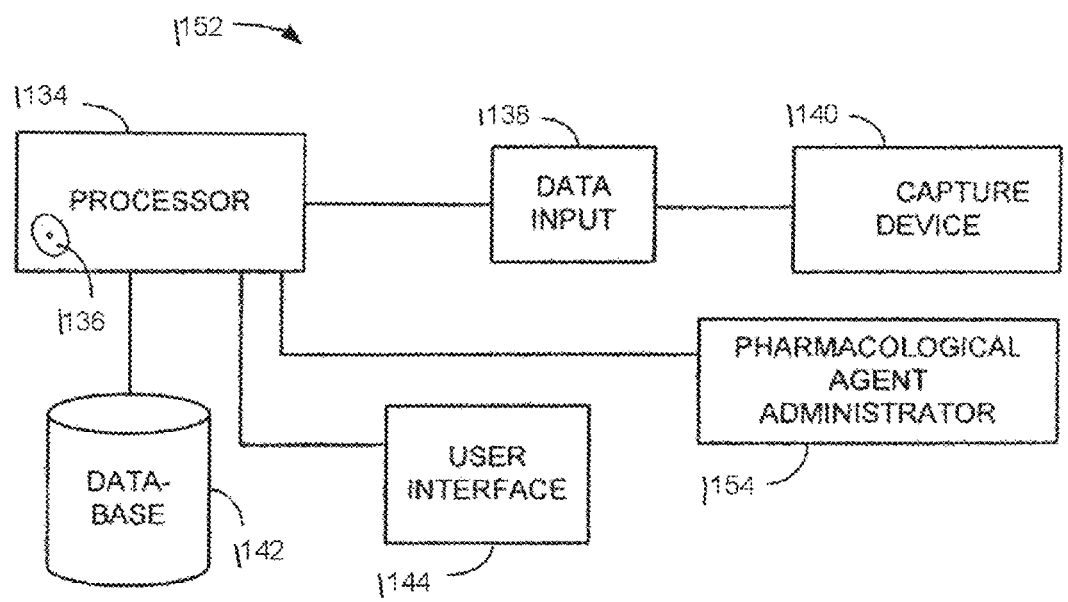

FIG. 12 schematically illustrates another embodiment of a system 1146 for evaluating an electrophysiological signal. In this embodiment, the processor 1134 is set-up to be a remote processor which is coupled to the data input 1138 over a network 1148. The network 1148 may be a wired or wireless local area network (LAN or WLAN) or the network 1148 may be a wired or wireless wide area network (WAN, WWAN) using any number of communication protocols to pass data back and forth. Having a system 1146 where the processor 1134 is located remotely allows multiple client side data inputs 1138 to share the resources of the processor 1134. Electrophysiological signals may be obtained by the data input 1138 from a database 1142 and/or an electrophysiological signal capture device 1140 under the control of a user interface 1144 coupled to the data input 1138. The electrophysiological signal may then be transferred over the network 1148 to the processor 1134 which can then identify a pathological substrate from a mathematical reconstruction of the electrophysiological signal (as described previously) and transmit data signals 1150 having the identified pathological condition to the client side. Such data transmissions may take place over a variety of transmission media, such as wired cable, optical cable, and air. In this embodiment, the remote processor 1134 can be used to help keep the cost of the client-side hardware down, and can facilitate any upgrades to the processor or the instructions being carried out by the processor, since there is a central upgrade point. FIG. 13 schematically illustrates a further embodiment of a system 1152 for evaluating an electrophysiological signal. In this embodiment, a data input 1138, a user interface 1144, and a database 1142 are coupled to the processor 1134. An electrophysiological signal capture device 1140 is coupled to the data input 1138. The system 1152 also has a pharmacological agent administrator 1154 which is coupled to the processor 1134. The pharmacological agent administrator 1154 may be configured to administer a pharmacological agent to a patient when enabled by the processor 1134. The system 1152 of FIG. 13, and its equivalents, may be useful in automating the analysis of the effectiveness of cardioactive agents or the cardiac toxicity of pharmacological agents on patients. Baseline cardiovascular characteristics can be identified from a mathematical reconstruction of an electrophysiological signal. Then, the processor 1134 can instruct the pharmacological agent administrator 1154 to administer a pharmacological agent. Then, analysis of cardioactive agents or the cardiac toxicity of pharmacological agents from a pre-administration and post-administration mathematical reconstruction of an electrophysiological signal. An effectiveness or cardiac toxicity of the pharmacological agent on may be determined based on a comparison of the baseline complex sub harmonic frequencies (CSF) and irrational fractional derivative and the post-administration CSF and irrational fractional subspace derivative magnitudes respectively.

Figure 14:
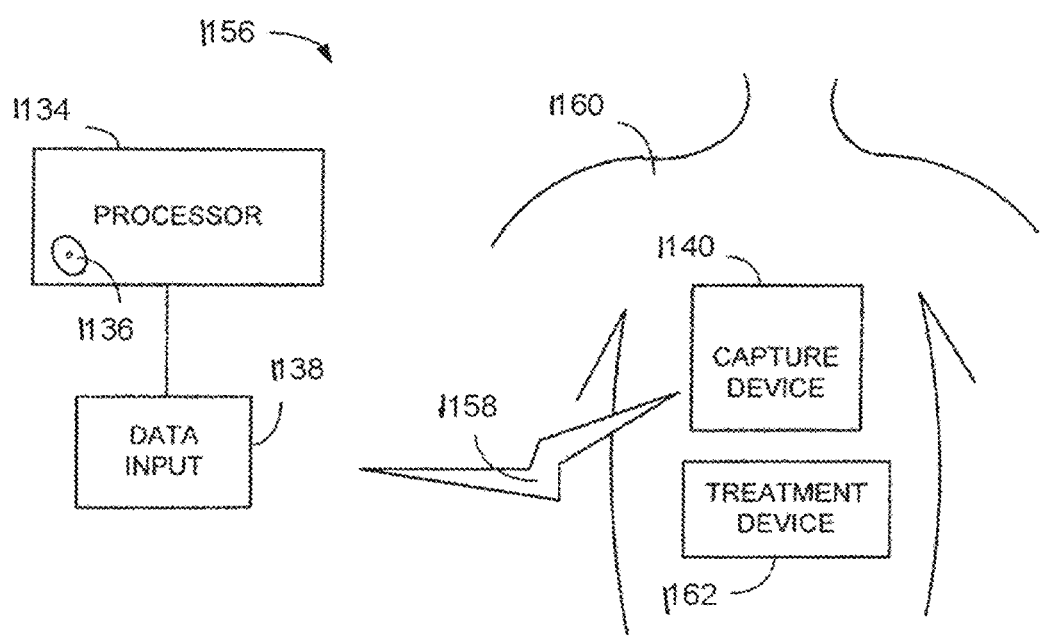

FIG. 14 schematically illustrates another embodiment of a system 1156 for evaluating an electrophysiological signal. Similar to other embodiments, the system has a processor 1134 which is coupled to a data input 1138. An electrophysiological signal capture device 1140 is coupled 1158 to the data input 1138. The coupling 1158 may be wired or wireless. The electrophysiological signal capture device 1140 is configured so that at least a portion of the electrophysiological signal capture device 1140 is implantable in a subject's body 1160. The processor 1134 and the data input 1138 are external to the subject's body 1160 in this embodiment, however, in other embodiments, the processor 1134 and/or the data input 1138 could be partially or entirely implanted in the subject's body 1160. The illustrated location of the implanted elements is merely for schematic illustration purposes and should not be considered limiting. The implanted elements may be located in any viable location of the body. The system 1156 of FIG. 14 may optionally have a treatment device 1162 coupled to the processor 1134. In this case, the processor 1134 may be configured to activate the treatment device 1162 to attempt to correct or forestall an unfavorable clinical pathological events identified for the patient. Suitable examples of treatment devices 1162 include, but are not limited to, a pharmacological agent administrator, a defibrillator, and an implantable body or brain device. The treatment device 1162 may also be partially or completely implanted inside of the subject 1160.

Noise Removal on a Z-Lead Using an MMP Model

The Discrete Fourier Transforms (DFT) is very good at producing a frequency distribution of power spectra for time series data. Unfortunately, when this technique is applied to biological time series data, which is inherently noisy, can be problematic since Fourier methods rely on equally spaced, complete data, and low noise for good characterization and cannot detect sub-harmonic frequencies. This is significant since these sub-harmonic frequencies exist in arrhythmia and are present proarrhythmic substrates when in sinus rhythm. To enhance the FFT, embodiments with our proposed use of the modified matching pursuit (MMP) method are better suited to encode and characterize electrophysiological signal data, such as electrocardiogram (ECG) data.

The key benefits of MMP over other Spectral Analysis programs are: 1) MMP achieves a higher spectral resolution, and 2) MMP makes use of a stopping criteria based on the least angle direction (LAD) and mean square error, therefore preventing the correlation of 'White Random Noise' that may be resident in the signal or signals being analyzed for key frequency content. MMP builds a functional expansion of an input signal by employing implicit orthogonal functions, "Orthogonal terms are fitted to minimize the candidate angle trajectory (LARS) and the mean square error of the orthogonal functional expansion." Subsequently, MMP then has a respective frequency resolution of up to twenty times of what the Discrete Fast Fourier Transform (DFT), or Wavelet method can yield, so notably, the MMP algorithm may play a critical role in sensitive detection systems that have to be able to select-out critical frequency signatures of interest and remove reoccurring noise. The MMPS algorithm creates frequency models of past detected highly correlated frequencies, and then compares the latest model against the most previous model. The comparison process continues until there is no energy left in the signal, and the subsequent mean square error values for both the orthogonal functions against a predetermined bottom threshold are met. The threshold is selected to prevent attempts to correlate unwanted biological signals or 'random noise' that may be present in the ECG signal.

Figure 15B:
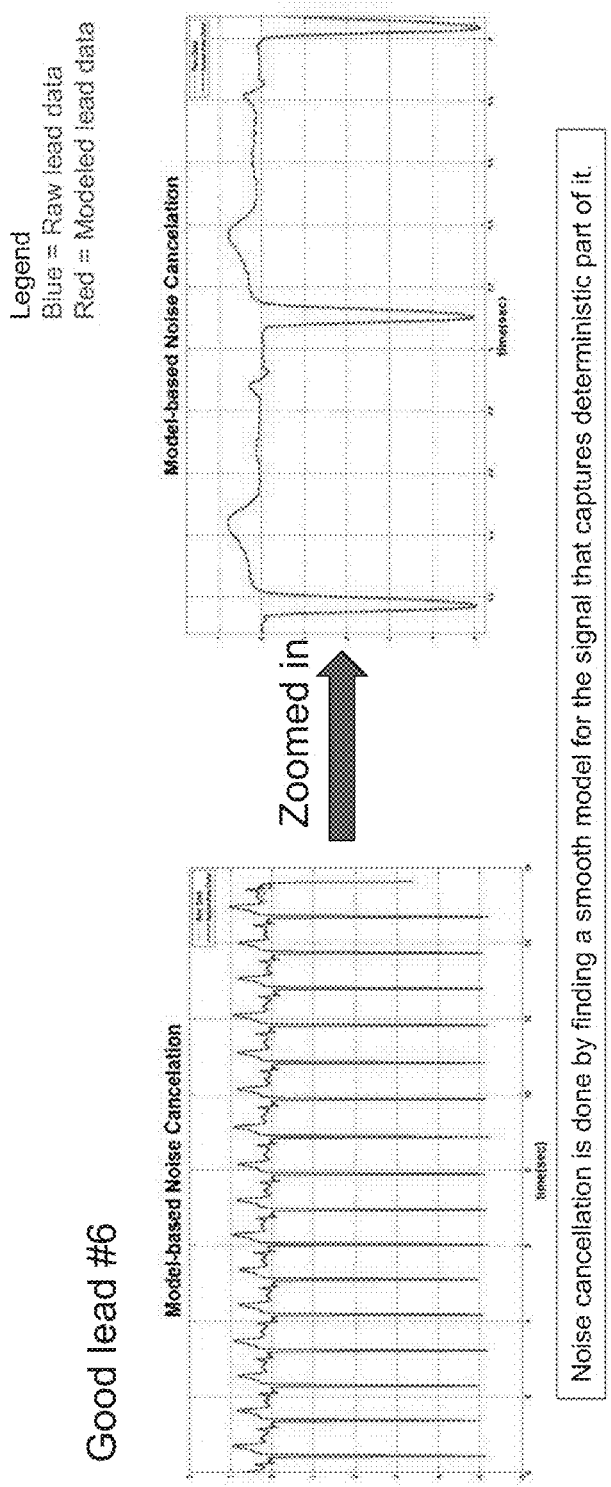

In addition, biological noise from breathing muscles and external noise and those from communication devices, switching power supplies, and terrestrial power lines can be detected and excluded or attenuated by customizing MMP. This can be done by identifying noise terms in the MMP models that are common to all ECG leads. These noise terms can be excluded from the MMP rebuilt signal as shown on the right-hand images of FIGS. 15A and 15B, where there is noise removal on one of the 12 leads using a MMP model (as compared to the left-hand images shown in FIGS. 15A and 15B before noise removal).

Applying the MMP algorithm to ECG data will provide an enhancement to the current clinic methods of using Wavelets and FFT, since this method can be customized to extract data from a surface ECG with a very high signal to noise ratio. A customized version of MMP has the potential to identify complex frequency components and sub components in anisotropic conduction, myocardial ischemia, channelpathies, atrial flutter, atrial fibrillation, ventricular tachycardia, and heart blocks with a vastly improved spectral response and noise rejection. This enhanced MMP model will provide a discrete-time and frequency model of the heart that may be used to confirm physical features of heart conduction.

Figure 16A:
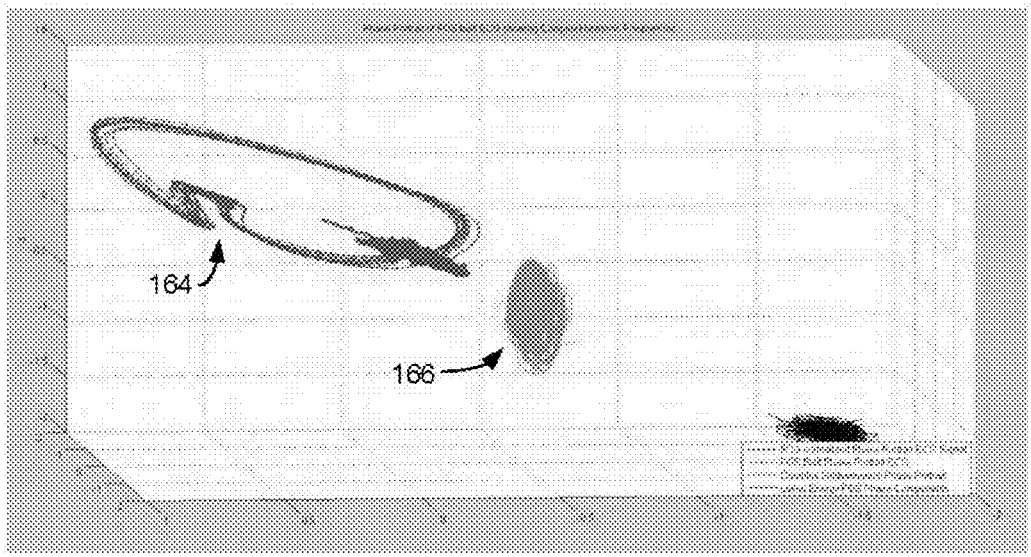
FIGS. 16A-16D illustrates Phase Portrait experimental data for a 14 year old girl with a large ventricular septal defect.
Figure 16B:
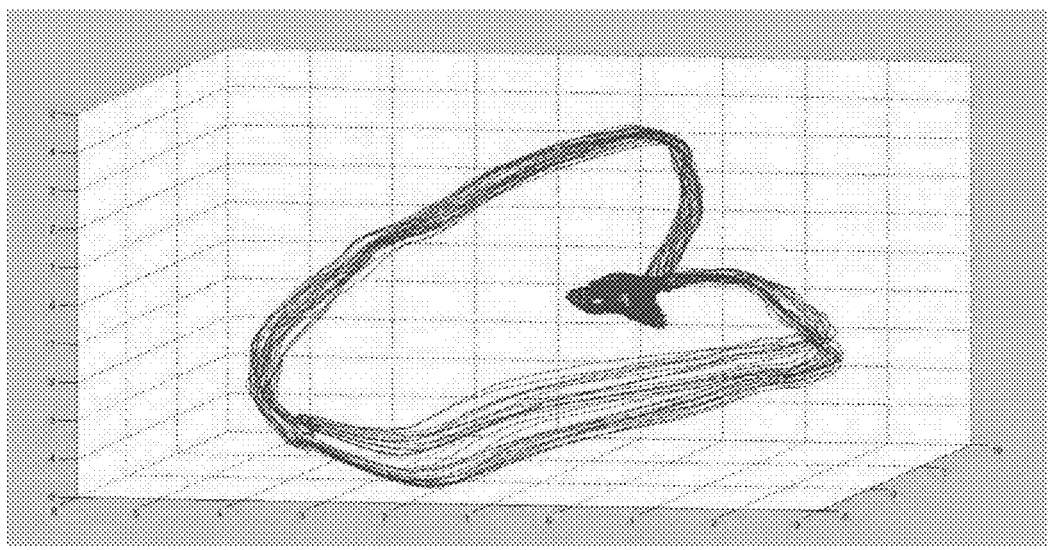
Figure 16C:
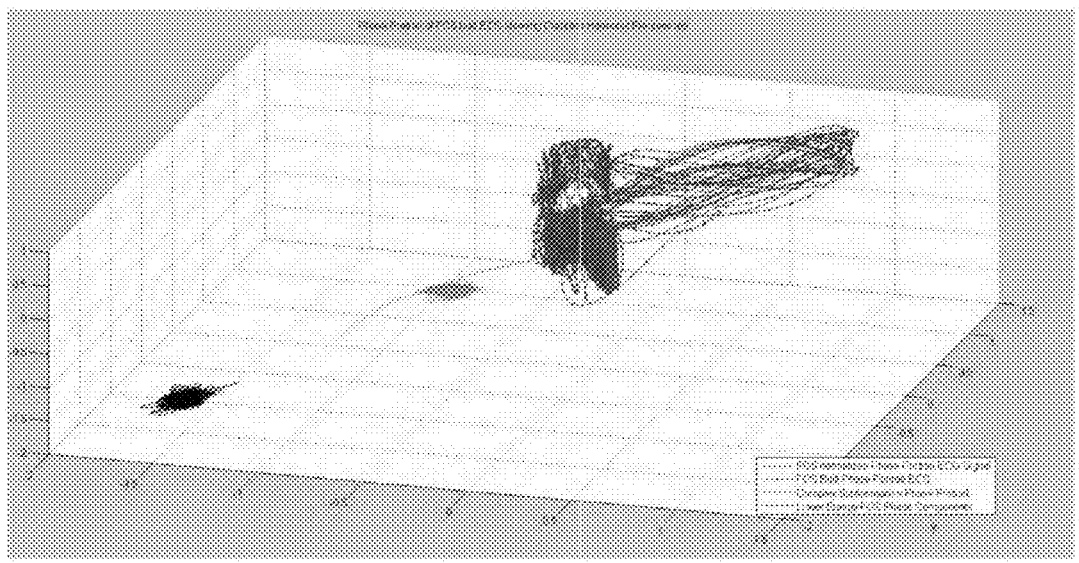
Figure 16D:
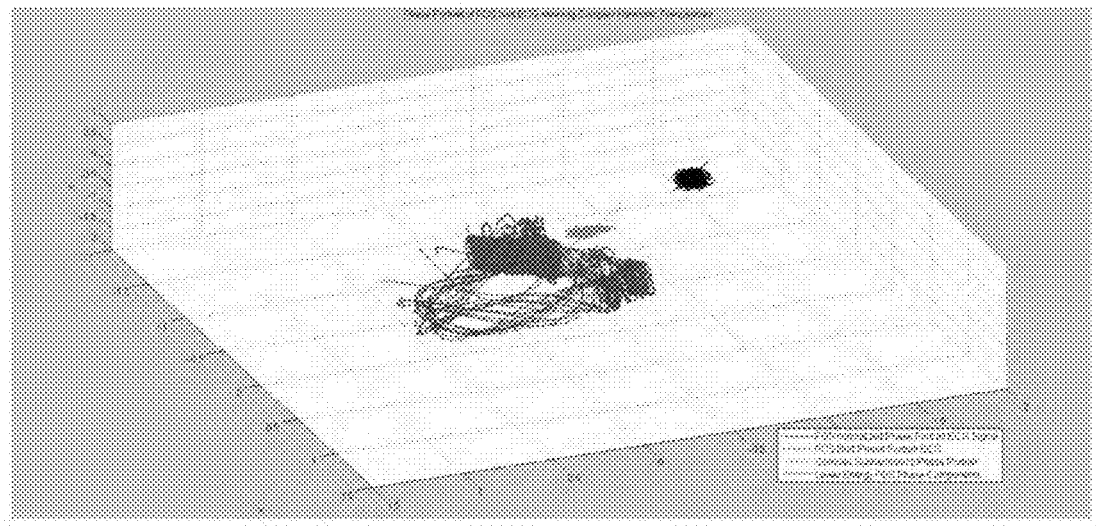

Experimental Results: Confirming Physical Features of Heart Conduction in Proarrhythmic Substrates when in Sinus Rhythm:

The disclosed methods and systems have provided valuable results when performed in real-world experiments. For example, FIG. 16A illustrates a Phase Portrait, produced using the methods disclosed herein to remove noise, for a 14 year old girl with a large ventricular septal defect. The septal defect can clearly be seen on the phase portrait of FIG. 16A. The electrophysiological signal (in this case, ECG data) was taken just after surgery to correct the septal defect. The tissue had not healed and the hole is still clearly showing as a notch 164 in the phase space portrait. The complex subharmonic region 166 has a tornadic shape which is a strong indicator of reentrant excitation (electrical whirlpool) around the newly corrected septal defect. Shortly after surgery she went into multiple episodes of ventricular tachycardia and was stabilized with medication. FIG. 16B shows the septal defect beginning to heal rapidly and show normal conduction. By comparison, FIGS. 16C and 16D show phase plots without the noise correction enabled with the methods disclosed herein, further complicated by the fact that the data was captured in part from a bad lead. It is next to impossible to make meaningful determinations from the phase space plots which were produced without the disclosed methods to remove the noise.

CONCLUSIONS

Myocardial infarction (MI) and its subsequent ventricular remodeling creates altered electrophysiological (EP) substrates that can be highly arrhythmogenic. Current noninvasive methods for assessing abnormal EP substrates rely on ECG measurements from the body surface potentials. Traditional methods cannot provide detailed EP information about the cardiac substrate. Intrinsic Phase Space ECG imaging (PSECGi), as disclosed herein, is a noninvasive computational method for reconstructing EP information on the heart surface from simple 3-lead orthogonal body surface measurements. Experimental and clinical data from infarcted hearts have helped to define measures for identifying abnormal EP substrates and for stratifying their arrhythmogenic potential. Identification of arrhythmogenic substrates before an arrhythmia occurs could reduce the risk of sudden death by indicating the need for a drug, device, or ablation therapy. An ICD study was used to evaluate the ability of PSECGi to noninvasively locate and characterize abnormal cardiac EP substrates associated with myocardial infarction. This technology can be extended for its application to patients with ischemic, congenital disease and other forms of cardiomyopathy in adults and examine its ability to detect and characterize abnormal hearts.

An automated method of reducing noise associated with electrophysiological signals is valuable in the determination of a pathological process. In some embodiments, MMP can be used to mathematically model ECG data and these terms have been used experimentally to reconstruct the ECG with great fidelity and compression (~30:1) while rejecting white noise without using filtering. This technique detected and rebuilt the original ECG's corrupted by 40% additive Gaussian noise. MMP can also be used as a selective nonlinear filter to remove terrestrial electromagnetic noise (e.g. 60 Hz line noise), stochastic noise and baseline drift that is common with ECG recordings associated with movement of the patient during recordings.

Transform an ECG into a vectrocardiogram (VCG): The standard ECG uses 12 leads positioned as it was found optimal from the medical point of view during a hundred years of practice. The VCG uses 3 channels connected in a orthogonal lead arrangement. LARS models can be used for converting 12-lead ECG into (3 orthogonal XYZ channels) 3-lead vectorcardiography, or vice versa. Traditionally this transform requires the use of algorithms like Karhunen-Loeve, Dower, and Levkov convert VCG to ECG. MMP based transformation provides efficient compression, white noise removal, and removal of baseline drift with lossless conversion of ECG into a vectrocardiogram (VCG), or vice versa.

Specific groups of mathematical MMP terms can be used to generate other subspaces of the 3D ECG signals. These subspaces are linked to specific properties of a non-linear system. In this case of ECG signals specific 3D subspaces have been linked to the determination of pathology. These subspace elements when quantified beat-to-beat in magnitude using a phase space clustering algorithm can be used to classify and predict heart arrhythmias and other heart abnormalities.

The influence of cardiac tissue architecture on conduction is determined by the packing of individual myocytes in three dimensions by size, shape, density and the genetic and physiological behavior of the specialized intercalated disks and gap junctions are responsible for the three dimensional time impulse propagation from cell to cell. This temporal spatial summation of the depolarization and repolarization of heart myocytes forms the surface ECG which is a multidimensional space time series of events. A novel way of characterizing a sequence of space time events in quasi-periodic systems is to take a long ECG and render it in multidimensional phase space where a point in space is a point in time. Long ECG records exhibit complex nonlinear variability that cannot be efficiently captured by traditional calculus or modeling techniques.

Figure 17:
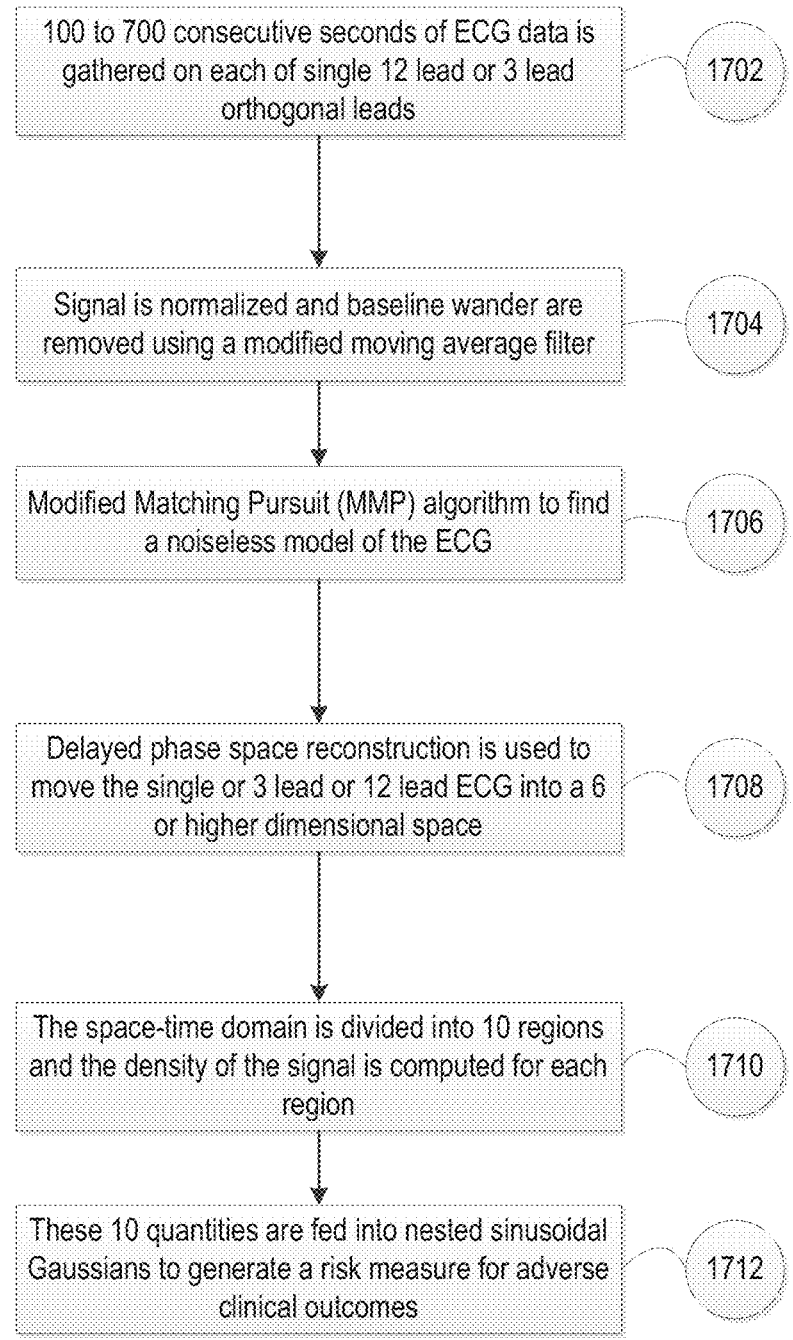
FIG. 17 illustrates an example process of generating other subspaces from groups of Modified Matching Pursuit (MPP) terms.

With reference to FIG. 17, the ECG signal is normalized and baseline wander is removed using a modified moving average filter (1702-1704). This signal is then modeled mathematically to included selected subspaces, over at least 100 seconds (1706), and transformed using delayed phase space reconstructions to increase the number of phase space dimensions to six or higher in order to extract informative high dimensional space time metrics (1708). Arrhythmogenensis in heart tissue, which is electrically and mechanical coupled excitable media, requires mathematical stability analysis for risk assessment. The occurrence of critical chaotic instabilities can be anticipated as future events by using stability analysis which reveals the generation and destruction of intermittent chaotic states. These unstable states increase the signal density in high dimensional space resulting in a strengthening of the strange attractor which can be linked to a pathological process intrinsic and extrinsic to the heart. The signal density in six dimensional space or higher is used to create 10 or more non-linear phase space cluster clouds (1710). These cluster clouds are agnostic to the traditional PQRST landmarks commonly used in clinical practice. The moment center is computed for the normalized six or higher dimensional ECG manifold. Cloud signal densities (SD) are a mixture of Gaussian sinusoidal functions that radiate from the moment center to the outer boundary of the manifold (1712). This allows for mixtures of Gaussian sinusoidal distributions to form complex decision boundaries that can be used to predict the risk for adverse clinical outcomes as shown in equation 1.

$$\text{RISK}=\text{gauss}(c_1(\text{SD}10+\text{SD}9+\text{SD}8)*\text{guass}(c_2*\text{SD}10-c_3*\sin(c_4-\text{SD}7-\text{guass}(\text{SD}5))))$$

$c$=real number constants   Equation 1

It should be valued that the specific example of equation 1 is for illustration and that various modifications can be made to the terms and mathematical structure without deviating from the spirit or scope of this disclosure.

Use MMP to compress the ECG: This compression ratio is calculated based on the number of points in the data versus the size of the frequency and amplitude array. It has been shown experimentally possible to compress the ECG with great fidelity at a ratio of 30 to 1. The brain is linked to the autonomic nervous system which amongst many systems in the body controls heart rate and cardiac output. Heart rate variability analysis traditionally requires observing variability of the R-R interval. Modified matching pursuit (MMP) can be used to model the entire signal 3D ECG data and this can be used to generate other subspaces of the 3D ECG signal which can replace traditional variability analysis. These subspaces are linked to specific properties of a parallel cascade of non-linear systems and as such can be used to model the states of the brain and the heart. More specifically the disclosed methods and associated apparatus for evaluating electrophysiological signals may sensitively and specifically predict current and future pathological events such as heart disease, diabetic autonomic neuropathy, cardiac arrhythmias, Parkinson's disease, epilepsy, brain injury/disorders and altered states of cognition such as bipolar disorder and attention deficit disorder (ADD).

MMP generated subspaces can be used to extract the fetal ECG from an ECG recorded on the mother's abdomen. The algorithm consists of two steps: first, ECG of fetus is extracted from the original signal using a 3D MMP transform, and then the Maternal ECG represents the remaining subspace energy.

Dynamical modeling of the 3D ECG will produce a moving 4D dynamical model of the 3D ECG using MMP to transform the signal into the Phase Space domain. This represents the ability to model the systems stability dynamically at different heart rates from the data collected from a resting ECG. ECG signal is transformed into variable time domain with higher or lower heart rates. Corresponding stability scores (Lyapunov exponent) may be recalculated to determine the maximum and minimum patient heart rate based on bifurcation maps.

FIGS. 18-24 illustrate various aspects of the present disclosure, including outputs, comparisons and results of the processes described above. FIG. 18 shows a MMP reconstructed Phase Portrait of a colored ECG vectorcardiogram showing regions of arrhythmogenic potential in red (circled regions). FIG. 19 illustrates an example of a formula generated (blue heart) 3D post MI heart with a lower anterior descending LAD) artery blockage. Ischemic and fibrotic tissue causes wave break-up or CSF and this can be seen as the large red territory which represents the ischemic downstream perfusion bed linked to the LAD occlusion. FIG. 20 illustrates an example of 3D vector annotated post MI heart with a lower anterior descending LAD) artery blockage. Ischemic and fibrotic tissue causes wave break-up or CSF and this can be seen as the large red territory which represents the ischemic downstream perfusion bed linked to the LAD occlusion. FIG. 21 shows a comparison between FOS reconstructed ECG waveform (red) and a native ECG waveform (blue). The FOS model uses more than 700 nonlinear terms to represent a 60 second ECG. The FOS built signal cannot mimic a 60 second ECG with 700 candidate terms, notice the amplitude and morphology differences between the native and FOS built signals.

FIG. 22 shows a magnified view comparison between FOS reconstructed ECG waveform (red) and a native ECG waveform (blue). The FOS model uses more than 700 nonlinear terms to represent a 60 second ECG. The FOS built signal cannot rebuild a complex 60 second ECG with 700 or more candidate terms. Amplitude and morphology differences are highlighted with blue circles/ellipses on the FOS built peaks. FIG. 23 shows a comparison between MMP reconstructed ECG waveform (red) and a native ECG waveform (blue). The MMP model uses ~700 nonlinear terms to represent an 800 second ECG. The MMP built signal can rebuild a complex 800 second ECG with ~700 candidate terms with a low MSE. FIG. 24 shows a magnified view comparison between MMP reconstructed ECG waveform (red) and a native ECG waveform (blue). The MMP model uses more than ~700 nonlinear terms to represent an 800 second ECG. The MMP built signal can rebuild a complex 800 second ECG with ~700 candidate terms. Amplitude and morphology differences are minor as the built signal mimics the native ECG signal.

Embodiments discussed have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed:

1. A method of evaluating an electrophysiological signal, comprising:

receiving an electrophysiological signal;

applying, using a processor of a computing device, a model-derived reconstruction using a summation series of complex exponentials over at least one cycle of the electrophysiological signal to identify a pathological substrate, the identification of the pathological substrate being based on a relative large or absolute value of the irrational fractional subspace derivative produced from the model-derived reconstruction of the electrophysiological signal; and displaying, on a user interface, one or more indicators of the electrophysiological signal to represent at least a portion of the electrophysiological signal and the pathological condition of the substrate and predict the risk for adverse clinical outcomes.

2. The method of claim 1, wherein the complex exponentials of the model-derived reconstruction of the electrophysiological signal comprises an input/output (I/O) expansion of the electrophysiological signal, in which at least one of the terms of the I/O expansion are fractionally differentiable and integrable.

3. The method of claim 2, wherein at least one term of the I/O expansion is Irrationally fractionally differentiable, and wherein the at least one term of the I/O expansion is analytically irrationally fractionally differentiable.

4. The method of claim 2, wherein the I/O expansion comprises a fractional derivative of order $\alpha$ that can be any real or complex number of the model-derived reconstruction.

5. The method of claim 1, wherein the accumulated absolute value of the irrational fractional subspace derivatives value indicate instability or arrhythmogenic potential, wherein the instability or arrhythmogenic potential is associated to a status of cardiac health including the risk of sudden death.

6. The method of claim 1, wherein the model-derived reconstruction which can include it's isolated subspaces of the electrophysiological signals over at least 100 seconds is transformed using delayed phase space reconstructions to increase the number of phase space dimensions to six or higher to extract informative high dimensional space time metrics, wherein cloud signal densities (SD), in high dimensional space, are a mixture of Gaussian sinusoidal functions that radiate from the moment center to the outer boundary of a manifold to allow for mixtures of Gaussian sinusoidal distributions to form complex decision boundaries that are used to predict a risk for adverse clinical outcomes, and wherein the Gaussian sinusoidal distributions are associated to a status of cardiac health including the risk of sudden death.

7. The method of claim 1, wherein the pathological substrate is selected from the group consisting of: a heart disease, a cardiac arrhythmia; a diabetic autonomic neuropathy; Parkinson's disease; a form of epilepsy; a brain injury; an altered state of cognition; a stability of a heart at different heart rates; an effectiveness of a medication; a measure of a toxicity of medication; an ischemia; a silent ischemia; a congenital heart defect; an atrial fibrillation; a ventricular fibrillation; a ventricular tachycardia; and a blood vessel blockage.

8. The method of claim 1, further comprising displaying on a user interface one or more indicators based on an input/output (I/O) expansion to represent at least a portion of the electrophysiological signal.

9. The method of claim 8, wherein the one or more indicators are displayed on one of a phase space plot and at least a portion of the electrophysiological signal.

10. The method of claim 1, wherein the one or more indicators are highlighted to further convey information about the pathological substrate identified from the complex exponential model-derived reconstruction of the electrophysiological signal.

11. The method of claim 1, wherein the highlighted indicators comprise at least one of color-coded indicators, shaded indicators, one or more types of a broken line, and one or more types of line thickness.

12. The method of claim 1, wherein the one or more indicators are displayed on a physiological image corresponding to the electrophysiological signal.

13. The method of claim 12, wherein the electrophysiological signal comprises an electrocardiogram (ECG) and the physiological image comprises an image of at least a portion of a heart.

14. The method of claim 12, wherein the electrophysiological signal comprises an electrocardiogram (ECG) and the physiological image comprises an image of at least a portion of a perfusion bed or the coronary artery circulation.

15. The method of claim 12, wherein the physiological image comprises a tissue image from a subject from whom the electrophysiological signal was obtained.

* * * * *